US010772513B2

United States Patent
Nakazawa et al.

(10) Patent No.: US 10,772,513 B2
(45) Date of Patent: Sep. 15, 2020

(54) BLOOD PRESSURE RATIO CALCULATION DEVICE, BLOOD PRESSURE RATIO CALCULATION METHOD, BLOOD PRESSURE RATIO CALCULATION PROGRAM, AND RECORDING MEDIUM RECORDING SAID PROGRAM

(71) Applicant: HAMAMATSU PHOTONICS K.K., Hamamatsu-shi, Shizuoka (JP)

(72) Inventors: Tomoya Nakazawa, Hamamatsu (JP); Rui Sekine, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 282 days.

(21) Appl. No.: 15/739,864

(22) PCT Filed: Mar. 8, 2016

(86) PCT No.: PCT/JP2016/057213
§ 371 (c)(1),
(2) Date: Dec. 26, 2017

(87) PCT Pub. No.: WO2017/002402
PCT Pub. Date: Jan. 5, 2017

(65) Prior Publication Data
US 2018/0184919 A1 Jul. 5, 2018

(30) Foreign Application Priority Data
Jul. 1, 2015 (JP) .................................. 2015-132525

(51) Int. Cl.
*A61B 5/021* (2006.01)
*A61B 5/00* (2006.01)
(Continued)

(52) U.S. Cl.
CPC .......... *A61B 5/02108* (2013.01); *A61B 5/022* (2013.01); *A61B 5/7257* (2013.01);
(Continued)

(58) Field of Classification Search
CPC ...... A61B 5/7257; A61B 5/021–02116; A61B 2560/0223–0238
See application file for complete search history.

(56) References Cited

U.S. PATENT DOCUMENTS 6,198,951 B1 * 3/2001 Kosuda .............. A61B 5/02416
600/323
6,293,915 B1 * 9/2001 Amano .................. A61B 5/021
600/485
(Continued)

FOREIGN PATENT DOCUMENTS

CN 1251027 A 4/2000
CN 101264011 A 9/2008
(Continued)

OTHER PUBLICATIONS

Pulse Pressure. Mar. 20, 2014. https://web.archive.org/web/20140320235542/https://en.wikipedia.org/wiki/Pulse_pressure (Year: 2014).*
(Continued)

*Primary Examiner* — Meredith Weare
(74) *Attorney, Agent, or Firm* — Faegre Drinker Biddle & Reath LLP

(57) ABSTRACT

A blood pressure ratio calculation device is a device for calculating a maximum-minimum blood pressure ratio corresponding to a ratio between a maximum blood pressure value and a minimum blood pressure value of an inspection target, and includes an input unit for inputting a relative blood pressure waveform corresponding to temporal change in relative blood pressure of the inspection target, a spectrum
(Continued)

generation unit for generating a relative blood pressure waveform spectrum by performing Fourier transform on the relative blood pressure waveform, and an analysis unit for calculating the maximum-minimum blood pressure ratio on the basis of the relative blood pressure waveform spectrum.

11 Claims, 14 Drawing Sheets

(51) Int. Cl.
    *A61B 5/022*     (2006.01)
    *A61B 5/02*     (2006.01)

(52) U.S. Cl.
    CPC .............. *A61B 5/002* (2013.01); *A61B 5/0059* (2013.01); *A61B 5/02007* (2013.01); *A61B 5/6898* (2013.01)

(56) References Cited

U.S. PATENT DOCUMENTS

2002/0161305 A1* 10/2002 Oka ...................... A61B 5/021
    600/490

2002/0177781 A1* 11/2002 Amano .................. A61B 5/021
    600/485
2017/0238816 A1* 8/2017 Nakazawa ............. A61B 5/022
2018/0353088 A1* 12/2018 Nakazawa .......... A61B 5/02108

FOREIGN PATENT DOCUMENTS

| | | |
|---|---|---|
| CN | 101288586 A | 10/2008 |
| CN | 103889319 A | 6/2014 |
| JP | H09-135819 A | 5/1997 |
| JP | 2002-325739 A | 11/2002 |
| JP | 2003-000555 A | 1/2003 |
| JP | 2004-154231 A | 6/2004 |
| JP | 2008-307307 A | 12/2008 |
| WO | WO-99/26529 A1 | 6/1999 |

OTHER PUBLICATIONS

International Preliminary Report on Patentability dated Jan. 11, 2018 for PCT/JP2016/057213.

* cited by examiner (a)

(b)

BLOOD PRESSURE RATIO CALCULATION DEVICE, BLOOD PRESSURE RATIO CALCULATION METHOD, BLOOD PRESSURE RATIO CALCULATION PROGRAM, AND RECORDING MEDIUM RECORDING SAID PROGRAM

TECHNICAL FIELD

An aspect of the present invention relates to a blood pressure ratio calculation device, a blood pressure ratio calculation method, a blood pressure ratio calculation program, and a recording medium having the program recorded thereon.

BACKGROUND ART

In the related art, a method of measuring a blood pressure waveform using a tonometer method using a pressure pulse wave sensor is known. In the method of measuring the blood pressure waveform using the tonometer method, relative change in arterial pressure can be measured. However, it is difficult to accurately obtain an absolute pressure of the arterial pressure. Therefore, it is necessary to calculate the absolute pressure of the arterial pressure by performing correction using a blood pressure value measured using a cuff. However, blood pressure waveform measurement using the tonometer method may not be able to be performed during the correction due to compression by the cuff. Therefore, for example, in a blood pressure waveform monitoring device described in Patent Literature 1, an estimated blood pressure waveform is acquired on the basis of a photoelectric pulse wave detected by a photoelectric pulse wave detection device during the correction, and the estimated blood pressure waveform is displayed instead of a relative blood pressure waveform measured by the tonometer method.

CITATION LIST

Patent Literature

[Patent Literature 1] Japanese Unexamined Patent Publication No. 2002-325739

SUMMARY OF INVENTION

Since a relative blood pressure waveform has values corresponding to relative temporal change in blood pressure and not absolute values, it is necessary to obtain an absolute blood pressure, a blood pressure waveform, or the like from the relative blood pressure waveform in order to accurately evaluate a cardiovascular system. However, in the technology described in Patent Literature 1 above, the relative blood pressure waveform acquired using the tonometer method must be corrected with the blood pressure values measured using a cuff in order to calculate the absolute pressure of the arterial pressure, and this is not convenient. Therefore, with the related art, it is difficult to evaluate the cardiovascular system conveniently, sufficiently, and accurately.

An aspect of the present invention is to provide a blood pressure ratio calculation device, a blood pressure ratio calculation method, and a blood pressure ratio calculation program capable of evaluating a cardiovascular system conveniently, sufficiently, and accurately.

Solution to Problem

In order to obtain absolute blood pressure, an absolute blood pressure waveform, or the like from a relative blood pressure waveform, it is necessary to clarify a relationship between a relative blood pressure waveform and an absolute blood pressure, an absolute blood pressure waveform, or the like. Therefore, the present inventors have conceived that a relationship between the spectrum of the relative blood pressure waveform and the maximum-minimum blood pressure ratio can be clarified and the maximum-minimum blood pressure ratio can be derived from the relative blood pressure waveform, thereby completing an aspect of the present invention, as a result of performing intensive research on a method of obtaining a ratio of a maximum blood pressure value to a minimum blood pressure value (hereinafter also referred to as a "maximum-minimum blood pressure ratio") indicating one relationship therebetween.

That is, an aspect of the present invention is a blood pressure ratio calculation device for calculating a maximum-minimum blood pressure ratio corresponding to a ratio between a maximum blood pressure value and a minimum blood pressure value of an inspection target, the device including: an input unit for inputting a relative blood pressure waveform corresponding to temporal change in relative blood pressure of the inspection target; a spectrum generation unit for generating a relative blood pressure waveform spectrum by performing Fourier transform on the relative blood pressure waveform; and an analysis unit for calculating the maximum-minimum blood pressure ratio on the basis of the relative blood pressure waveform spectrum.

Further, another aspect of the present invention is a blood pressure ratio calculation method of calculating a maximum-minimum blood pressure ratio corresponding to a ratio between a maximum blood pressure value and a minimum blood pressure value of an inspection target, the blood pressure ratio calculation method including: an input step of inputting a relative blood pressure waveform corresponding to temporal change in relative blood pressure of the inspection target; a spectrum generation step of generating a relative blood pressure waveform spectrum by performing Fourier transform on the relative blood pressure waveform; and an analysis step of calculating the maximum-minimum blood pressure ratio on the basis of the relative blood pressure waveform spectrum.

Yet another aspect of the present invention is a program for causing a computer to execute a process of calculating a maximum-minimum blood pressure ratio corresponding to a ratio of a maximum blood pressure value to a minimum blood pressure value of an inspection target, the program causing a computer to function as: an input unit for inputting a relative blood pressure waveform corresponding to temporal change in relative blood pressure of the inspection target; a spectrum generation unit for generating a relative blood pressure waveform spectrum by performing Fourier transform on the relative blood pressure waveform; and an analysis unit for calculating the maximum-minimum blood pressure ratio on the basis of the relative blood pressure waveform spectrum. Further, yet another aspect of the present invention is a computer-readable recording medium having the blood pressure ratio calculation program recorded thereon.

In the blood pressure ratio calculation device, the blood pressure ratio calculation method, the blood pressure ratio calculation program, and the recording medium having the program recorded thereon according to the embodiment of the present invention, the maximum-minimum blood pressure ratio of the inspection target is calculated on the basis of the relative blood pressure waveform spectrum generated by performing Fourier transform on the relative blood pressure waveform. Since the calculated maximum-minimum blood pressure ratio indicates one relationship between the relative blood pressure waveform and the absolute blood pressure, the absolute blood pressure waveform, or the like, it is possible to obtain the absolute blood pressure waveform from the relative blood pressure waveform using the maximum-minimum blood pressure ratio, or to use the calculated maximum-minimum blood pressure ratio as an evaluation indicator of a cardiac function. Therefore, by calculating the maximum-minimum blood pressure ratio on the basis of the relative blood pressure waveform, it is possible to evaluate the cardiovascular system conveniently and accurately.

Advantageous Effects of Invention

According to an aspect of the present invention, a blood pressure ratio calculation device, a blood pressure ratio calculation method, a blood pressure ratio calculation program, and a recording medium having the program recorded thereon capable of evaluating a cardiovascular system conveniently, sufficiently, and accurately are provided.

DESCRIPTION OF EMBODIMENTS

Figure 1:
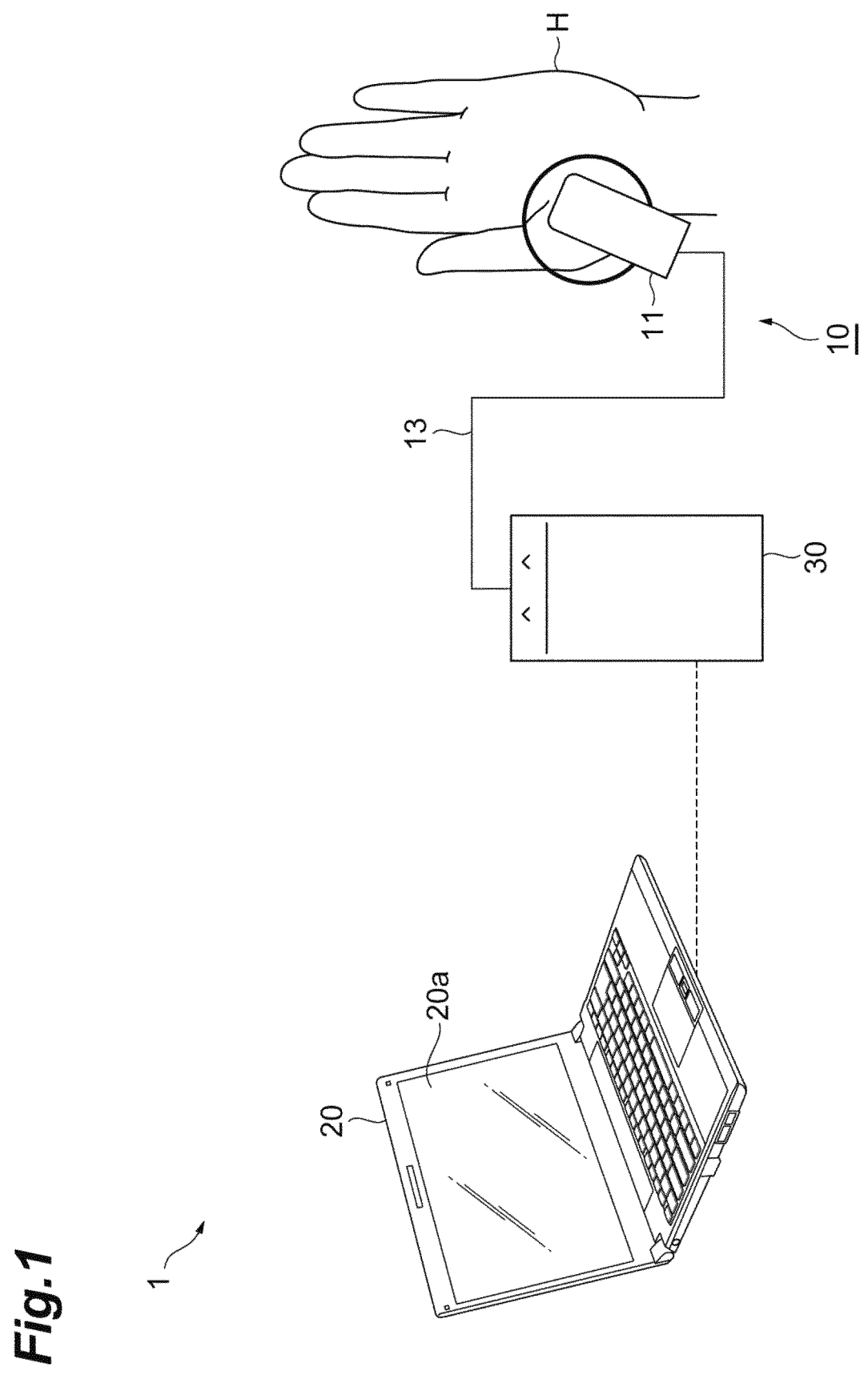
FIG. 1 is a schematic configuration diagram illustrating an absolute blood pressure waveform calculation system including a blood pressure ratio calculation device according to a first embodiment of an aspect of the present invention.

Hereinafter, embodiments of an aspect of the present invention will be described in detail with reference to the accompanying drawings. In the description, the same elements or elements having the same functions are denoted with the same reference numerals, and repeated description thereof will be omitted.

First Embodiment

First, an overview of an absolute blood pressure waveform calculation system including a blood pressure ratio calculation device according to a first embodiment of an aspect of the present invention will be described. The absolute blood pressure waveform calculation system according to this embodiment is a system that calculates an absolute blood pressure waveform from a relative blood pressure waveform of an inspection target (subject). The relative blood pressure waveform is information corresponding to temporal change in relative blood pressure of the subject. The relative blood pressure waveform can be acquired by, for example, a Near Infra-Red Spectroscopy (NIRS) device, a pulse oximeter, a tonometer, or the like. For example, in the NIRS device, by irradiating a living body with light and detecting an intensity of reflected light from the living body, change in blood volume over time occurring at a predetermined position in the living body is measured from a surface of the living body, and a result thereof is acquired as a relative blood pressure waveform (photoelectric pulse wave). In the pulse oximeter, oxygen saturation of arterial blood is measured, and a result thereof is acquired as the relative blood pressure waveform. In the tonometer, a relative change in arterial pressure is measured by a blood pressure sensor attached to a radial artery or the like using a blood vessel wall motion due to blood pressure fluctuation, and a result thereof is acquired as the relative blood pressure waveform. Further, the relative blood pressure waveform may be acquired by, for example, plethysmography, an electromagnetic blood flow meter, an ultrasonic blood flow meter, a laser blood flow meter, or the like. In this embodiment, a case in which a photoelectric pulse wave acquired by an NIRS device is used as a relative blood pressure waveform will be described.

A relative blood pressure waveform has a correspondence relationship with a blood pressure waveform (hereinafter also referred to as a "true blood pressure waveform") in which temporal change in an absolute value of blood pressure in an artery is taken as a waveform. The relative blood pressure waveform has values different from the true blood pressure waveform, but has a shape similar to a shape of the true blood pressure waveform. The absolute blood pressure waveform calculation system calculates the maximum-minimum blood pressure ratio corresponding to the ratio between the maximum blood pressure value and the minimum blood pressure value of the subject calculated on the basis of the relative blood pressure waveform, and reproduces the true blood pressure waveform by calculating the absolute blood pressure waveform from the relative blood pressure waveform on the basis of the calculated maximum-minimum blood pressure ratio. The maximum blood pressure value is a systolic blood pressure value that becomes highest in a systole, and the minimum blood pressure value is a diastolic blood pressure value that becomes lowest in a diastole. The absolute blood pressure waveform is information corresponding to temporal change in the absolute value of the blood pressure (that is, values of the blood pressure itself), and is a waveform corresponding to the true blood pressure waveform.

Figure 2:
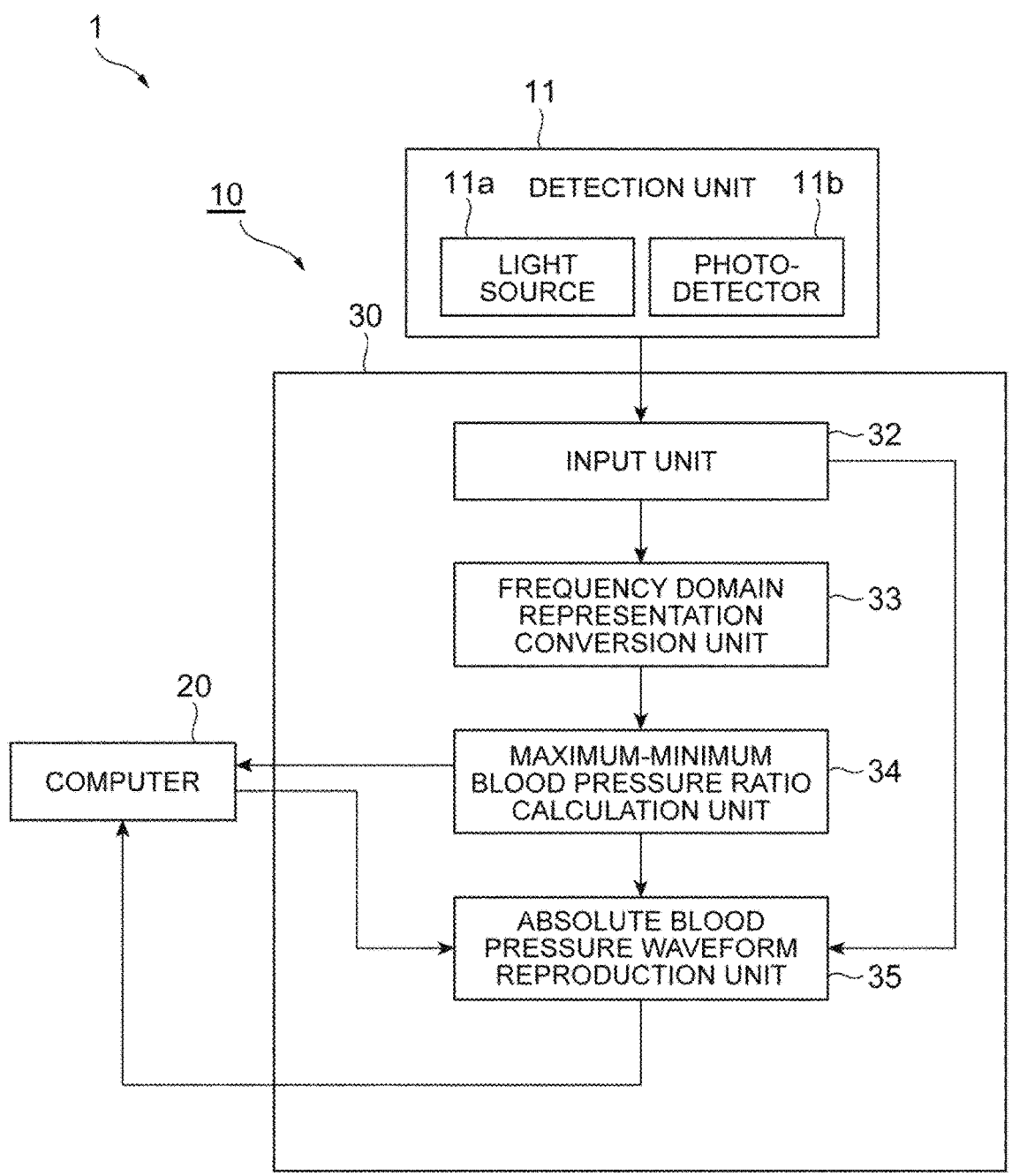
FIG. 2 is a functional block diagram of a processing unit in FIG. 1.

FIG. 1 is a schematic configuration diagram illustrating an absolute blood pressure waveform calculation system including a blood pressure ratio calculation device according to a first embodiment of an aspect of the present invention. FIG. 2 is a functional block diagram of a processing unit in FIG. 1. As illustrated in FIG. 1, the absolute blood pressure waveform calculation system 1 includes a relative blood pressure waveform acquisition device 10 (blood pressure ratio calculation device), and a computer 20.

The relative blood pressure waveform acquisition device 10 acquires a photoelectric pulse wave as a relative blood pressure waveform in a living body as a subject, for example, using near-infrared spectroscopy (NIRS). Further, the relative blood pressure waveform acquisition device 10 calculates a maximum-minimum blood pressure ratio of the subject on the basis of the acquired relative blood pressure waveform. As the relative blood pressure waveform acquisition device 10, for example, a portable near-infrared tissue oxygen monitor device may be used. The relative blood pressure waveform acquisition device 10 includes a detection unit 11 (acquisition unit), and a processing unit 30.

The detection unit 11 detects a signal for acquiring the relative blood pressure waveform. The detection unit 11 has a form of a probe that comes into contact with a surface (in this embodiment, a palm of a hand) of a living body H that is a subject. The detection unit 11 includes a light source 11a (irradiation device) and a photodetector 11b (see FIG. 2). The detection unit 11 radiates near-infrared light from the light source 11a from the surface of the living body H to the inside thereof, and detects reflected light from the inside of the living body H using the photodetector 11b. Accordingly, the detection unit 11 acquires an absorbance when the light passes through the inside of the living body H. Since this absorbance changes according to a blood volume at a contact position of the detection unit 11 in the living body H, temporal change in this absorbance corresponds to a photoelectric pulse wave. Examples of components that absorb light in the blood include red blood cells, hemoglobin contained in red blood cells, and moisture. The detection unit 11 detects the photoelectric pulse wave and acquires the photoelectric pulse wave as a relative blood pressure waveform. The detection unit 11 is electrically connected to the processing unit 30 via a cable 13, and transmits the acquired relative blood pressure waveform to the processing unit 30 via the cable 13. That is, the detection unit 11 is an acquisition unit that acquires the relative blood pressure waveform and inputs the relative blood pressure waveform to the processing unit 30.

The processing unit 30 receives the relative blood pressure waveform from the detection unit 11. The processing unit 30 calculates a maximum-minimum blood pressure ratio by executing a predetermined process on the basis of the input relative blood pressure waveform. The predetermined process will be described below in detail. The relative blood pressure waveform is known to be influenced by viscoelastic characteristics of a blood vessel. The viscoelastic characteristics of the blood vessel are characteristics indicating a behavior of viscoelasticity of the blood vessel, that is, both elasticity and viscosity in the blood vessel. Therefore, a similar blood pressure waveform in which the influence is reduced by correcting the input relative blood pressure waveform using a viscoelastic characteristics correction value indicating the viscoelastic characteristics of the blood vessel may be acquired, and the maximum-minimum blood pressure ratio may be calculated by performing the predetermined process based on the similar blood pressure waveform as the relative blood pressure waveform.

Further, the processing unit 30 calculates the absolute blood pressure waveform from the relative blood pressure waveform using the calculated maximum-minimum blood pressure ratio. The processing unit 30 calculates the absolute blood pressure waveform by performing a predetermined process of correcting a magnification, a reference point, and the like on the relative blood pressure waveform on the basis of the maximum-minimum blood pressure ratio. The processing unit 30 transmits the calculated absolute blood pressure waveform to the computer 20 using wireless communication or the like. Further, the processing unit 30 may transmit the calculated maximum-minimum blood pressure ratio to the computer 20 using wireless communication or the like, together with or instead of the absolute blood pressure waveform.

In the predetermined process in the processing unit 30, the processing unit 30 calculates the absolute blood pressure waveform by correcting the relative blood pressure waveform using feature points of the blood pressure waveform of the subject and the maximum-minimum blood pressure ratio. For example, a feature point may be a dicrotic notch point, an average blood pressure value, or the like. In this embodiment, a case in which, for example, a dicrotic notch point is used as a feature point will be described. Here, the dicrotic notch point (hereinafter referred to as a "notch point") is a point of change (dicrotic notch) in blood pressure caused by an aortic valve closing due to a decrease in a blood volume. Since a blood pressure value at a moment when the aortic valve closes depends only on a magnitude of a predetermined initial load, the blood pressure value at the notch point can be assumed to be substantially constant for each subject irrespective of an exercise state of the subject. On the basis of this assumption, the processing unit 30 uses the blood pressure value at the notch point in the blood pressure waveform of the subject calculated or measured in advance for the process. The processing unit 30 acquires information indicating the notch point such as a blood pressure value at the notch point in the blood pressure waveform of the subject calculated or measured in advance according to an input from the computer 20, for example. The predetermined process in the processing unit 30 will be described below in detail.

The computer 20 stores the information indicating the notch point in the blood pressure waveform of the subject calculated or measured in advance, and transmits the information indicating the notch point to the processing unit 30 using wireless communication or the like. Further, the computer 20 receives information indicating the absolute blood pressure waveform from the processing unit 30 using wireless communication or the like. The computer 20 includes a display unit such as a display 20a, and displays the received information indicating the absolute blood pressure waveform on the display 20a. Further, the computer 20 may receive information indicating the maximum-minimum blood pressure ratio from the processing unit 30 using wireless communication or the like. The computer 20 may display the received information indicating the maximum-minimum blood pressure ratio on the display 20a together with or instead of the information indicating the absolute blood pressure waveform. The computer 20 and the relative blood pressure waveform acquisition device 10 may be electrically connected by a cable or the like, and the computer 20 may receive information from the processing unit 30 using wired communication.

As illustrated in FIG. 2, the processing unit 30 includes an input unit 32, a frequency domain representation conversion unit (spectrum generation unit) 33, a maximum-minimum blood pressure ratio calculation unit (analysis unit) 34, and an absolute blood pressure waveform reproduction unit 35 (blood pressure waveform calculation unit).

The input unit 32 receives a relative blood pressure waveform P' from the detection unit 11. The input unit 32 outputs information on the input relative blood pressure waveform P' to the frequency domain representation conversion unit 33 and the absolute blood pressure waveform reproduction unit 35.

The frequency domain representation conversion unit 33 is a spectrum generation unit that generates a relative blood pressure waveform spectrum P'$_F$ by performing Fourier transform on the relative blood pressure waveform P' input by the input unit 32. That is, the frequency domain representation conversion unit 33 converts the relative blood pressure waveform P' that is a function of time indicated in a time domain representation into a relative blood pressure waveform spectrum P'$_F$ that is a function of a frequency indicated in a frequency domain representation. The frequency domain representation conversion unit 33 outputs information on the generated relative blood pressure waveform spectrum P'$_F$ to the maximum-minimum blood pressure ratio calculation unit 34. The frequency domain representation conversion unit 33 may correct the input relative blood pressure waveform P' using a viscoelastic characteristics correction value indicating viscoelastic characteristics of the blood vessel to acquire a similar blood pressure waveform in which an influence of the viscoelastic characteristics of the blood vessel has been reduced, and perform Fourier transform on this similar blood pressure waveform as the relative blood pressure waveform P' to generate a relative blood pressure waveform spectrum.

The maximum-minimum blood pressure ratio calculation unit 34 calculates a maximum-minimum blood pressure ratio P$_{Tmax}$:P$_{Tmin}$ of the subject on the basis of the relative blood pressure waveform spectrum P'$_F$ at a frequency equal to or higher than a frequency corresponding to the pulse of the subject in the relative blood pressure waveform spectrum P'$_F$ generated by the frequency domain representation conversion unit 33. Specifically, the maximum-minimum blood pressure ratio calculation unit 34 calculates the maximum-minimum blood pressure ratio P$_{Tmax}$:P$_{Tmin}$ on the basis of the following Equation (1). Equation (1) indicates a statistically significant correspondence relationship that has been newly found as a result of repeated intensive research of the present inventors. The correspondence relationship and Equation (1) will be described below in detail.

[Math. 1]

$$P_{T\ min} : P_{T\ max} = |P'_F(f_1)| : \sum_{n=1}^{N} |P'_F(f_n)| \quad (1)$$

Here, in Equation (1), n represents a positive integer, $f_1$ represents a frequency corresponding to the pulse, and $f_n$ represents a frequency n times the frequency corresponding to the pulse.

Hereinafter, a wave at the frequency $f_1$ corresponding to the pulse in the relative blood pressure waveform spectrum P'$_F$ is set as a first harmonic wave, and a wave at a frequency $f_n$ which is n times the frequency $f_1$ of the first harmonic wave is set as an n-th harmonic wave. The frequency $f_1$ corresponding to the pulse is in a frequency range corresponding to a pulse that a human body can take, such as about 0.5 Hz to 3.7 Hz. The frequency $f_1$ corresponding to the pulse fluctuates within the frequency range (about 0.5 Hz to 3.7 Hz) corresponding to the pulse that the human body can take due to fluctuations in the living body, and the frequency $f_n$ also fluctuates accordingly. In Equation (1) above, P'$_F$($f_1$) indicates the spectral intensity of the first harmonic wave, and P'$_F$($f_n$) indicates the spectral intensity of the n-th harmonic wave. The spectral intensity of the first harmonic wave is, for example, the peak value of the spectral intensity of the first harmonic wave, and the spectral intensity of the n-th harmonic wave is, for example, the peak value of the spectral intensity of the n-th harmonic wave.

The maximum-minimum blood pressure ratio calculation unit 34 calculates the maximum-minimum blood pressure ratio P$_{Tmax}$:P$_{Tmin}$ by calculating a ratio of a sum of respective peak values of the spectral intensities of the first harmonic wave or a higher harmonic wave in the relative blood pressure waveform spectrum P'$_F$ to a peak value of the spectral intensity of the first harmonic wave in the relative blood pressure waveform spectrum P'$_F$ on the basis of Equation (1) above. The maximum-minimum blood pressure ratio calculation unit 34, for example, may set N=3 when calculating the maximum-minimum blood pressure ratio P$_{Tmax}$:P$_{Tmin}$ according to Equation (1) above. That is, the peak values of the spectral intensity of at least the first harmonic wave to the third harmonic wave may be used. Further, the maximum-minimum blood pressure ratio calculation unit 34 may set N=6. That is, the peak values of the spectral intensity of the first harmonic wave to the sixth harmonic wave may be used. Further, more specifically, since a component at a frequency higher than 30 Hz in the relative blood pressure waveform spectrum P'$_F$ is noise, a peak value of the spectral intensity of 30 Hz or lower may be used so that such noise is not reflected in the calculation result and, preferably, a peak value of the spectral intensity of 20 Hz or lower is used. The maximum-minimum blood pressure ratio calculation unit 34 outputs the calculated maximum-minimum blood pressure ratio P$_{Tmax}$:P$_{Tmin}$ to the absolute blood pressure waveform reproduction unit 35. The maximum-minimum blood pressure ratio calculation unit 34 may output the calculated maximum-minimum blood pressure ratio P$_{Tmax}$:P$_{Tmin}$ to the computer 20.

Further, the maximum-minimum blood pressure ratio calculation unit 34 may calculate the maximum-minimum blood pressure ratio P$_{Tmax}$:P$_{Tmin}$ on the basis of a sum of intensities of the respective relative blood pressure waveform spectra of the first harmonic wave group or a higher harmonic wave group. Specifically, the maximum-minimum blood pressure ratio calculation unit 34 may calculate the maximum-minimum blood pressure ratio P$_{Tmax}$:P$_{Tmin}$ on the basis of Equation (2) below. Equation (2) indicates a statistically significant correspondence relationship that has been newly found as a result of repeated intensive research of the present inventors. The correspondence relationship and Equation (2) will be described below in detail.

[Math. 2]

$$P_{T\ min} : P_{T\ max} = \int_{-d}^{d} \left| P'_F\left(f_1 + \frac{f}{2}\right) \right| df : \sum_{n=1}^{N} \int_{-d}^{d} \left| P'_F\left(f_a + \frac{f}{2}\right) \right| df \quad (2)$$

Here, in Equation (2), n represents a positive integer, $f_1$ represents a frequency corresponding to the pulse, and $f_n$ represents a frequency n times the frequency corresponding to the pulse.

Figure 9:
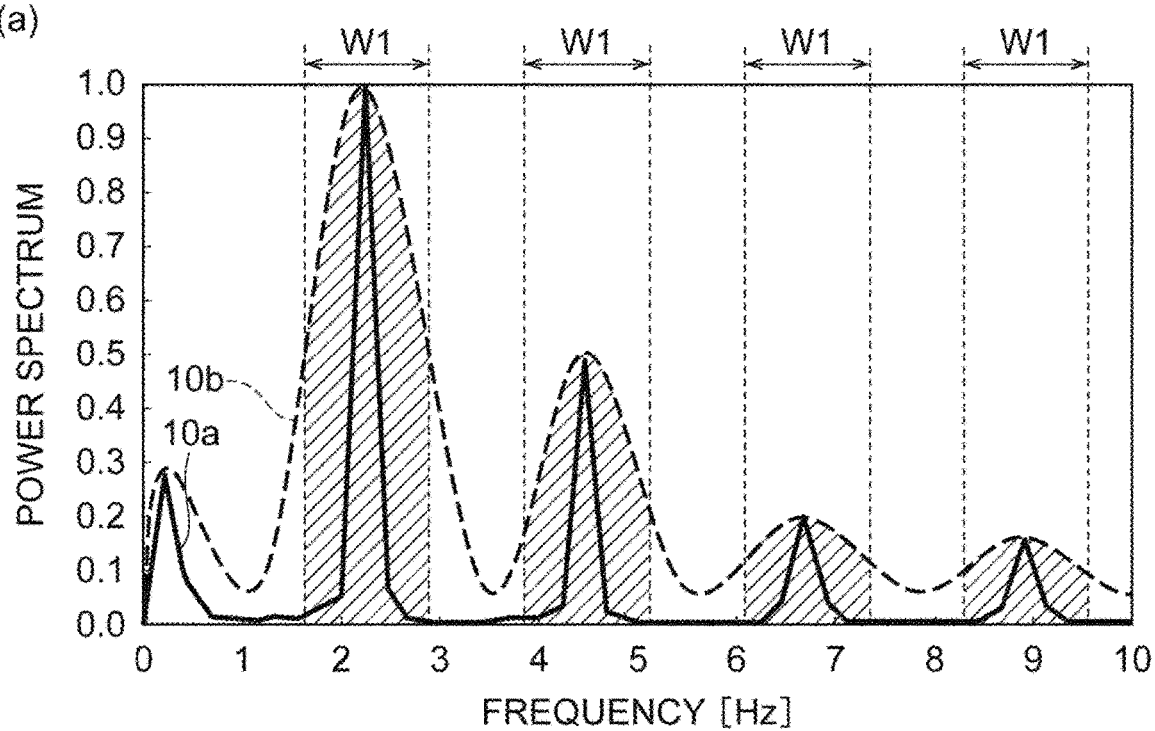
FIG. 9 is a diagram illustrating an effective width of a spectral intensity of the power spectrum illustrated in FIG. 8.
Figure 9:
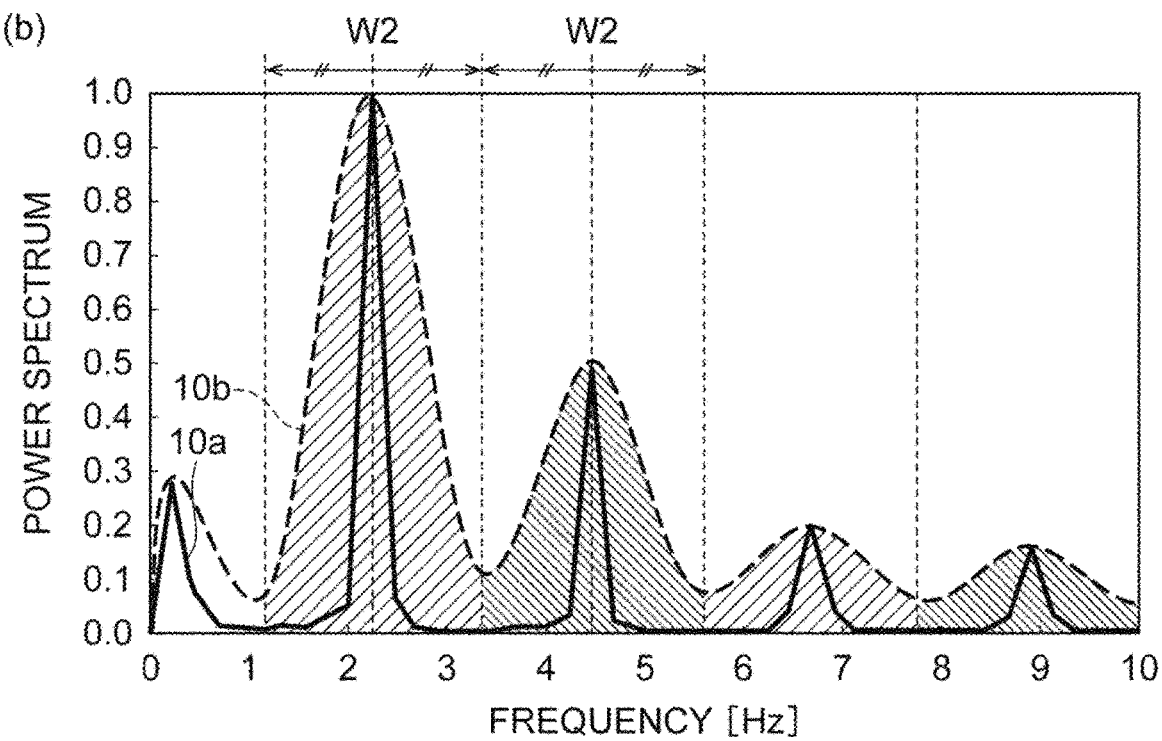

Hereinafter, a group of waves at a frequency in a predetermined range of the frequency $f_1$ corresponding to the pulse, including the frequency $f_1$ corresponding to the pulse, is set as the first harmonic wave group. More specifically, the first harmonic wave group is, for example, a spectrum in a range with a predetermined effective width around a peak value of a spectral intensity of the first harmonic wave. The spectral intensity of the first harmonic wave group is, for example, an integral value of the spectral intensity in a predetermined effective width. Further, a group of waves at a frequency in a predetermined range of a frequency $f_n$, including the frequency $f_n$ which is n times the frequency $f_1$ corresponding to the pulse, is set as an n-th harmonic wave group. More specifically, the n-th harmonic wave group is, for example, a spectrum in a range with a predetermined effective width around a peak value of the spectral intensity of the n-th harmonic wave. The spectral intensity of the n-th harmonic wave group is, for example, an integral value of the spectral intensity in a predetermined effective width. A specific example of the predetermined effective width will be described below with reference to FIG. 9.

On the basis of Equation (2) above, the maximum-minimum blood pressure ratio calculation unit 34 may calculate the maximum-minimum blood pressure ratio $P_{Tmax}:P_{Tmin}$ by calculating a ratio of a sum of the respective peak values of the spectral intensities of the first harmonic wave group or a higher harmonic wave group in the relative blood pressure waveform spectrum $P'_F$ to the peak value of the spectral intensity of the first harmonic wave group in the relative blood pressure waveform spectrum $P'_F$. The maximum-minimum blood pressure ratio calculation unit 34 may set N=3 in Equation (2) above. That is, the integral value of the spectral intensity of at least the first harmonic wave group to the third harmonic wave group may be used. Further, the maximum-minimum blood pressure ratio calculation unit 34 may set N=6. That is, the integral value of the spectral intensity from the first harmonic wave group to the sixth harmonic wave group may be used. Further, more specifically, since a component at a frequency higher than 30 Hz in the relative blood pressure waveform spectrum $P'_F$ is noise, an integral value of a spectral intensity of 30 Hz or lower may be used such that noise is not reflected in a calculation result and, preferably, an integral value of a spectral intensity of 20 Hz or lower may be used.

The absolute blood pressure waveform reproduction unit 35 calculates the absolute blood pressure waveform on the basis of the maximum-minimum blood pressure ratio $P_{Tmax}:P_{Tmin}$ calculated by the maximum-minimum blood pressure ratio calculation unit 34. Here, the relative blood pressure waveform P' has values different from the true blood pressure waveform, but has a shape similar to a shape of the true blood pressure waveform. The relative blood pressure waveform P' has a minimum point corresponding to a minimum blood pressure value $P_{Tmin}$ that is diastolic blood pressure in the true blood pressure waveform, a maximum point corresponding to a maximum blood pressure value $P_{Tmax}$ that is a systolic blood pressure in the true blood pressure waveform, and a reference point corresponding to a feature point (notch point) in the true blood pressure waveform. The minimum point in the relative blood pressure waveform P', for example, is detected as a point at which the waveform intensity becomes smallest in the relative blood pressure waveform P', and the maximum point in the relative blood pressure waveform P', for example, is detected as a point at which the waveform intensity becomes greatest in the relative blood pressure waveform P'. Since the reference point in the relative blood pressure waveform P' corresponds to a dicrotic notch in the true blood pressure waveform and indicates a point of change in the waveform, the reference point can be detected, for example, as in a method of detecting an extreme value. By differentiating the relative blood pressure waveform P' with respect to time, the reference point may be clearer and be easy to detect.

First, the absolute blood pressure waveform reproduction unit 35 corrects the magnification in the relative blood pressure waveform P' output from the input unit 32 on the basis of the maximum-minimum blood pressure ratio $P_{Tmax}:P_{Tmin}$ calculated by the maximum-minimum blood pressure ratio calculation unit 34. Specifically, the absolute blood pressure waveform reproduction unit 35 detects a minimum point and a maximum point in the relative blood pressure waveform P', calculates a ratio between the detected minimum point and the detected maximum point, and adds an addition coefficient to the relative blood pressure waveform P' or multiplies the relative blood pressure waveform P' by a multiplication coefficient so that the ratio is substantially the same as the maximum-minimum blood pressure ratio $P_{Tmax}:P_{Tmin}$ to correct the magnification in the relative blood pressure waveform P'. Thus, the magnification-corrected relative blood pressure waveform is calculated.

Then, the absolute blood pressure waveform reproduction unit 35 acquires the blood pressure value at the notch point using the output from the computer 20, corrects the reference point in the magnification-corrected relative blood pressure waveform obtained by performing the magnification correction as described above with the blood pressure at the notch point, and calculates the absolute blood pressure waveform. Specifically, the absolute blood pressure waveform reproduction unit 35 detects the reference point in the magnification-corrected relative blood pressure waveform, and corrects the reference point in the magnification-corrected relative blood pressure waveform by adding an addition coefficient to the magnification-corrected relative blood pressure waveform or multiplying the magnification-corrected relative blood pressure waveform by a multiplication coefficient so that the waveform value of the detected reference point is substantially equal to the blood pressure value at the notch point. For example, when the blood pressure value at the notch point is about 90 mmHg, the waveform value of the reference point detected in the magnification-corrected relative blood pressure waveform is corrected to be about 90 mmHg. Accordingly, the absolute blood pressure waveform $P_T$ is calculated. The absolute blood pressure waveform reproduction unit 35 outputs the calculated absolute blood pressure waveform $P_T$ to the computer 20.

Figure 3:
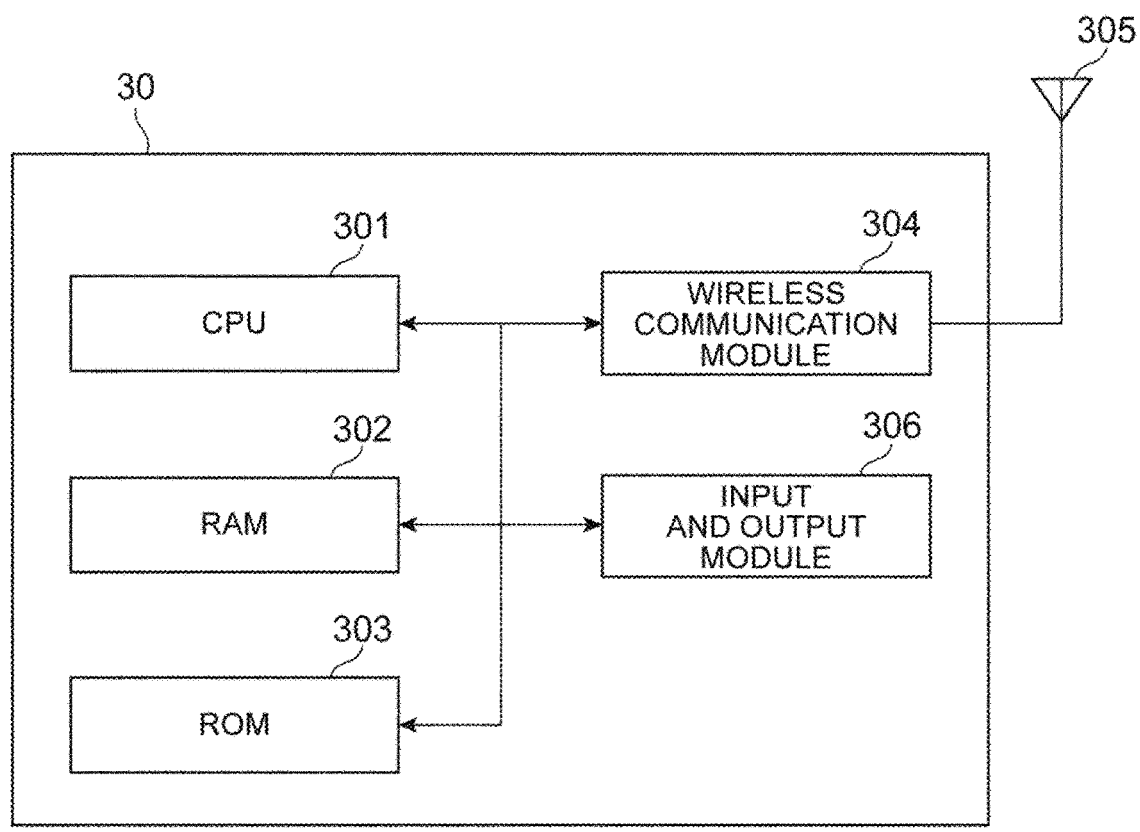
FIG. 3 is a diagram illustrating a hardware configuration of the processing unit in FIG. 1.

Next, a hardware configuration of the processing unit 30 will be described with reference to FIG. 3. FIG. 3 illustrates a hardware configuration of the processing unit 30 in FIG. 1. As illustrated in FIG. 3, the processing unit 30 physically is a computer including, for example, a central processing unit (CPU) 301 that is a processor, a random access memory (RAM) 302 or a read only memory (ROM) 303 that is a recording medium, a wireless communication module 304, an antenna 305, and an input and output module 306, which are electrically connected. Each function of the processing unit 30 described above is realized by operating, for example, the wireless communication module 304, the antenna 305, and the input and output module 306 under control of the CPU 301 by loading the blood pressure ratio calculation program or the like on hardware such as the CPU 301 and the RAM 302, and performing reading and writing of data in the RAM 302. The processing unit 30 may include a display, an operation module, or the like.

Next, the correspondence relationship shown in Equation (1) above discovered by the present inventors will be described in detail.

Figure 4:
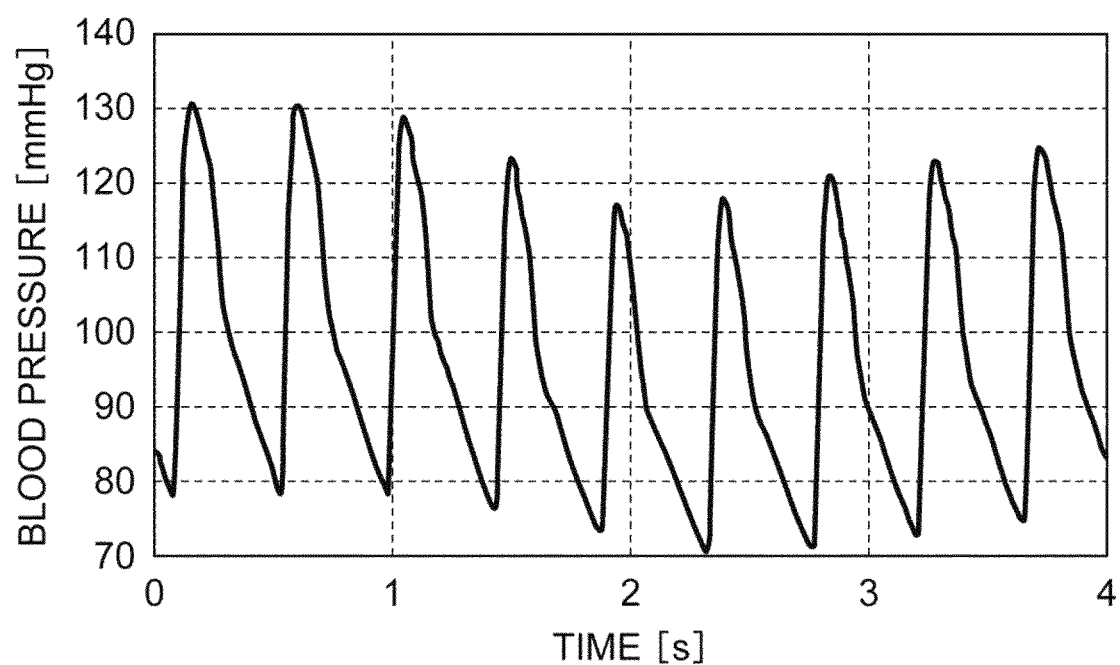
FIG. 4 is a graph showing a true blood pressure waveform measured by an invasive catheter sphygmomanometer.

FIG. 4 is a graph showing a true blood pressure waveform measured by an invasive catheter sphygmomanometer. A horizontal axis of FIG. 4 indicates time [s], and a vertical axis of FIG. 4 indicates blood pressure [mmHg]. In the graph illustrated in FIG. 4, the maximum blood pressure value $P_{Tmax}$ is about 130 mmHg and the minimum blood pressure value $P_{Tmin}$ is about 70 mmHg. Therefore, a ratio between the maximum blood pressure value $P_{Tmax}$ and the minimum blood pressure value $P_{Tmin}$, that is, the maximum-minimum blood pressure ratio is about 1.86. The blood pressure waveform mainly includes a first harmonic wave (main wave) at the frequency $f_1$ corresponding to the pulse, and an n-th harmonic wave at the frequency $f_n$ higher than the frequency $f_1$. When the blood pressure waveform illustrated in FIG. 4 is subjected to Fourier transform, a power spectrum as illustrated in FIG. 5 is obtained.

Figure 5:
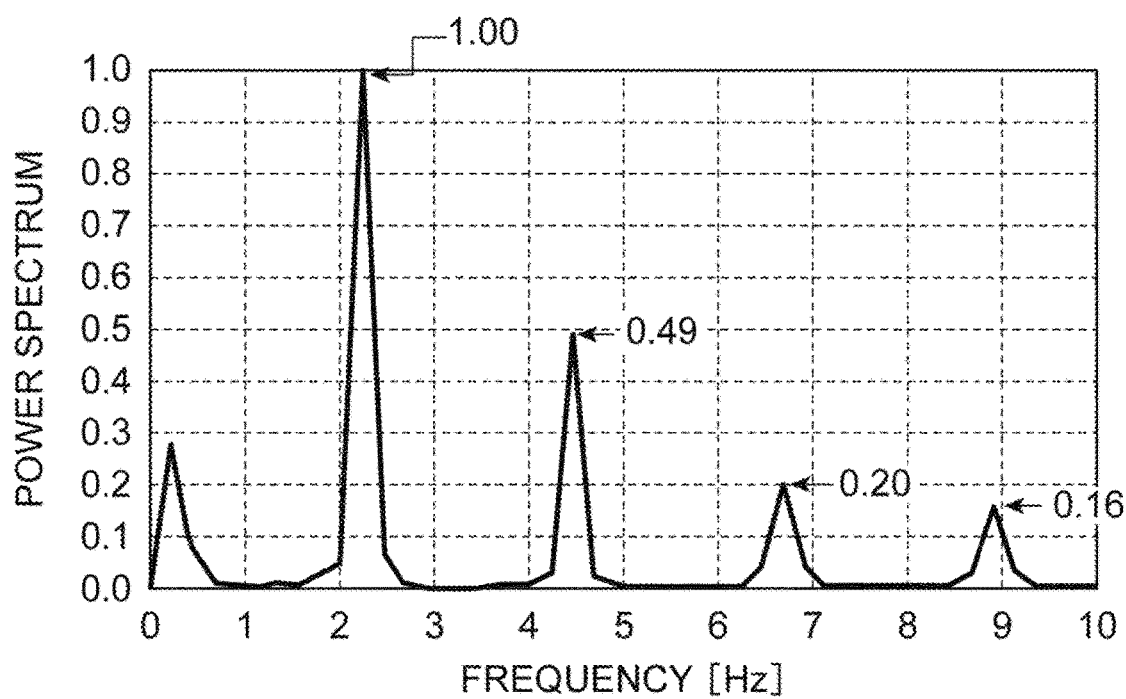
FIG. 5 is a graph showing a power spectrum of the blood pressure waveform illustrated in FIG. 4.

FIG. 5 is a graph showing a power spectrum obtained by performing Fourier transform on the blood pressure waveform illustrated in FIG. 4. The power spectrum is normalized using a spectral intensity of the first harmonic wave. A horizontal axis of FIG. 5 indicates a frequency [Hz], and a vertical axis of FIG. 5 indicates the spectral intensity. As a result of intensive research, the present inventors have found that in the power spectrum illustrated in FIG. 5, a ratio of the sum of the spectral intensities of the n-th harmonic wave that is the first harmonic wave or a higher harmonic wave to the intensity of the spectrum of the first harmonic wave (hereinafter referred to as a "ratio based on a spectral intensity") is substantially equal to the maximum-minimum blood pressure ratio obtained from the blood pressure waveform illustrated in FIG. 4. Specifically, in the power spectrum illustrated in FIG. 5, a sum of the spectral intensities of the n-th harmonic wave that is the first harmonic wave or a higher harmonic wave is 1.00+0.49+0.20+0.16=1.85. Therefore, the ratio of the sum of the spectral intensities of the n-th harmonic wave that is the first harmonic wave or a higher harmonic wave to the spectral intensity of the first harmonic wave is 1.85 and is substantially equal to about 1.86 that is the ratio of the maximum blood pressure value $P_{Tmax}$ and the minimum blood pressure value $P_{Tmin}$ in the true blood pressure waveform. This correspondence relationship can be expressed by Equation (1) above.

Figure 6:
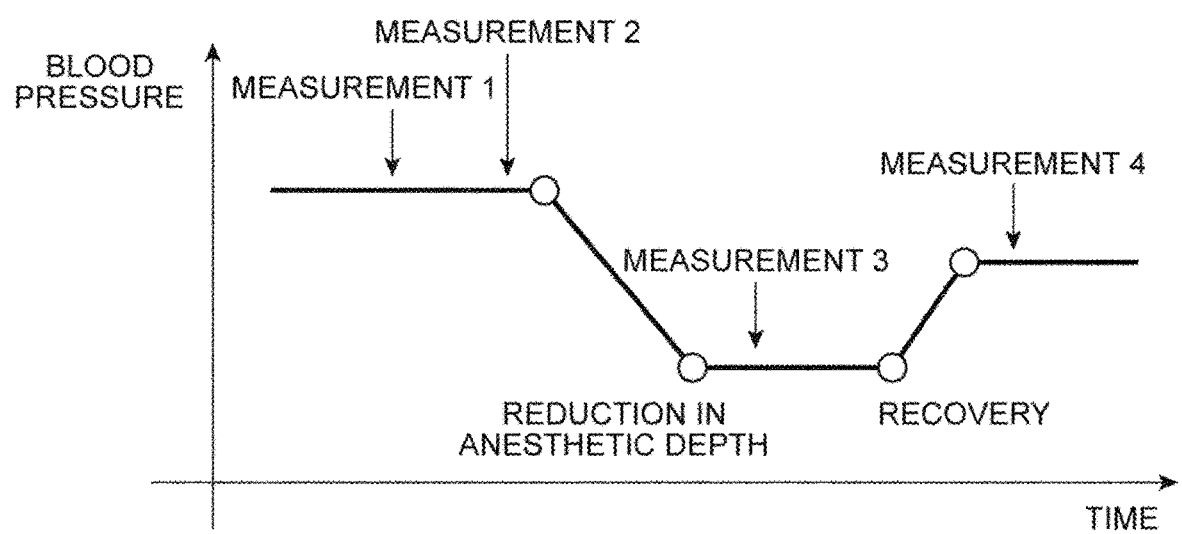
FIG. 6 is a graph showing fluctuation in blood pressure of a cynomolgus monkey due to an anesthetic agent.

The present inventors have confirmed that the correspondence relationship shown in Equation (1) above is statistically significant from the following experiment. The present inventors have continuously measured a blood pressure waveform indicating fluctuation in blood pressure of a cynomolgus monkey while applying an isoflurane anesthetic agent having different concentrations to the cynomolgus monkey and causing the blood pressure to fluctuate in a state in which an invasive sphygmomanometer is installed in an artery of a foot of the cynomolgus monkey. FIG. 6 illustrates fluctuation in blood pressure of the cynomolgus monkey due to the anesthetic agent. In FIG. 6, a horizontal axis indicates time and a vertical axis of FIG. 6 indicates blood pressure.

Figure 7:
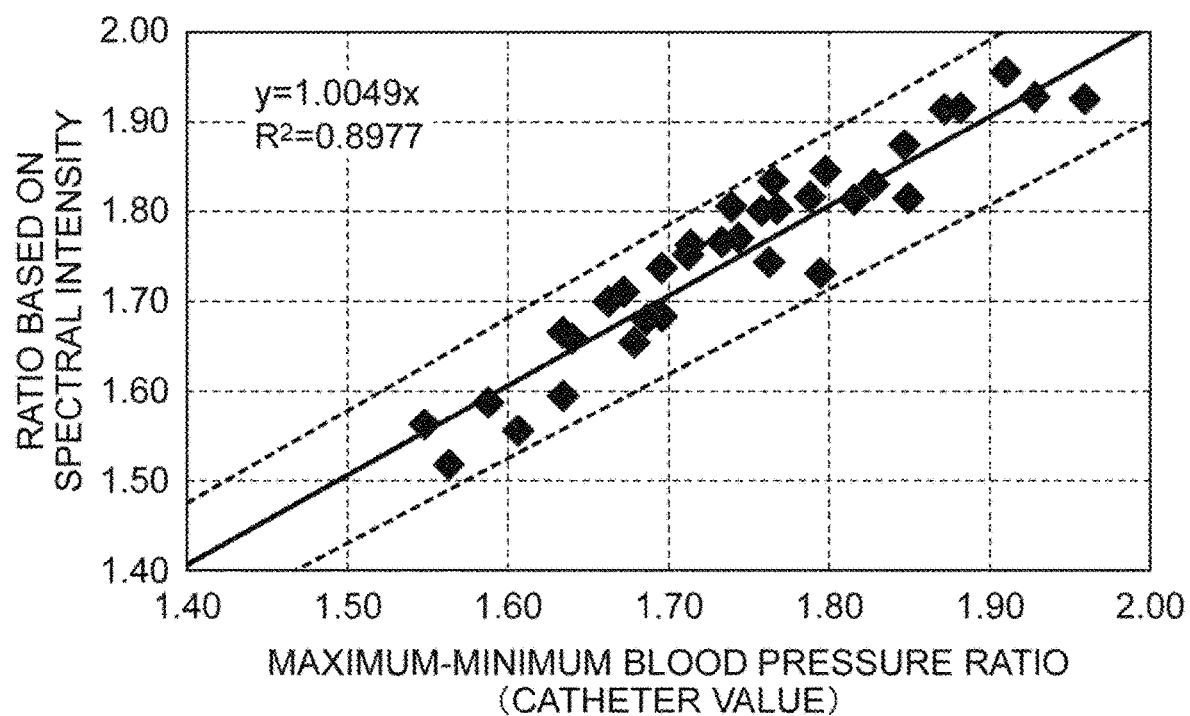
FIG. 7 is a graph showing a correlation between a maximum-minimum blood pressure ratio and a ratio based on a spectral intensity of a blood pressure waveform.

A plurality of pieces of data in different time periods in the measured blood pressure waveform were extracted, and a relationship between the ratio between the maximum blood pressure and the minimum blood pressure obtained from the extracted data and the ratio based on the spectral intensity obtained by performing Fourier transform on the blood pressure waveform was plotted as illustrated in the graph of FIG. 7, and a correlation thereof has been confirmed. A horizontal axis of FIG. 7 indicates the maximum-minimum blood pressure ratio obtained by an experiment performed on the cynomolgus monkey, and a vertical axis of FIG. 7 indicates the ratio based on the spectral intensity obtained by performing Fourier transform on the blood pressure waveform. As illustrated in FIG. 7, the ratio based on the spectral intensity obtained by performing Fourier transform on the blood pressure waveform has been confirmed to fall within a range of ±5% of the ratio between the maximum blood pressure and the minimum blood pressure obtained by the experiment performed on the cynomolgus monkey.

The above shows that the correspondence relationship represented by Equation (1) above is statistically significant.

The precision of the relationship shown in Equation (1) above depends on a frequency resolution of the Fourier transform. When one pulse wave is considered, ideally, there are no waves other than integer multiple harmonic waves of a frequency corresponding to the pulse. However, when a plurality of pulse waves are considered, waves other than the integer multiple harmonic waves of the frequency corresponding to the pulse are included due to biological fluctuations.

In principle, the frequency resolution due to the Fourier transform depends on a length of a time waveform before the transform, but since an actually measured time waveform has a finite length, a spectrum of the time waveform cannot be completely separated for each frequency. The spectrum of each integer multiple harmonic wave includes a spectrum of a peripheral wave other than an integer multiple harmonic wave. When the frequency resolution is higher, waves other than an integer multiple harmonic wave can be removed, and the accuracy of the relationship shown in Equation (1) above is improved. Conversely, when the frequency resolution is lower, the accuracy is degraded under an influence of waves other than an integer multiple harmonic wave. Although there is a difference in accuracy according to the frequency resolution of the Fourier transform, the correspondence relationship shown in Equation (1) above remains statistically significant.

Figure 8:
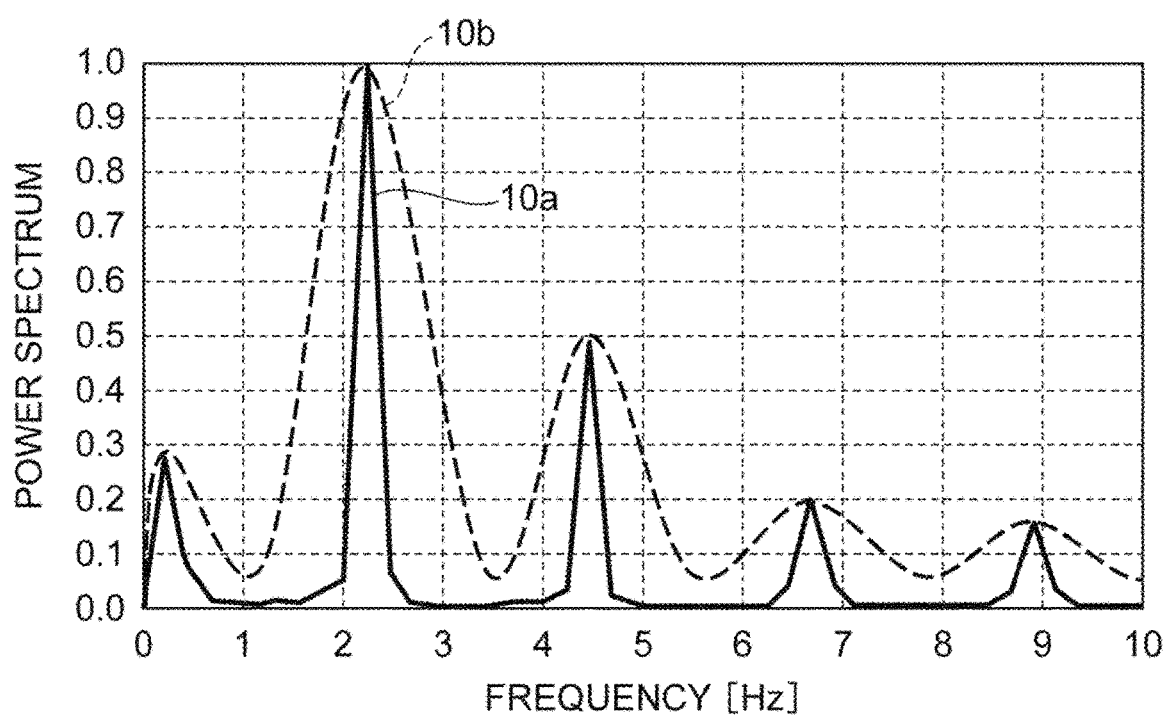
FIG. 8 is a graph showing spreading of a power spectrum of a blood pressure waveform due to biological fluctuations.

FIG. 8 is a graph showing spreading of a power spectrum of the blood pressure waveform due to biological fluctuations. A horizontal axis of FIG. 8 indicates a frequency [Hz], and a vertical axis of FIG. 8 indicates the spectral intensity. A graph 10a in FIG. 8 shows a power spectrum of an ideal blood pressure waveform in which biological fluctuations are ignored, and a graph 10b in FIG. 8 shows a power spectrum of a blood pressure waveform including waves other than an integer multiple harmonic wave due to biological fluctuations. The graph 10b showing the power spectrum of the blood pressure waveform including waves other than an integer multiple harmonic wave due to biological fluctuations has a wider peak for each peak than the graph 10a showing the power spectrum of the ideal blood pressure waveform in which biological fluctuations are ignored.

The present inventors have found that in the power spectrum of the blood pressure waveform including waves other than an integer multiple harmonic wave due to biological fluctuations, the ratio of the sum of the spectral intensities of the n-th harmonic wave group that is the first harmonic wave group or a higher harmonic wave group to the spectral intensity of the first harmonic wave group is substantially equal to the ratio between the maximum blood pressure value $P_{Tmax}$ and the minimum blood pressure value $P_{Tmin}$. That is, the inventors have found that the correspondence relationship expressed by Equation (2) above is satisfied.

By establishing the correspondence relationship shown in Equation (2) above, it is possible to obtain the maximum-minimum blood pressure ratio from the integral value of the spectral intensity in the predetermined effective width including each peak value, as described above. Here, the predetermined effective width may be, for example, a frequency width W1 which corresponds to a half value of the peak value of the spectral intensity of the n-th harmonic wave as illustrated in FIG. 9(a) or may be, for example, a frequency width W2 separated at a center between frequencies of adjacent n-th harmonic waves as illustrated in FIG. 9(b). An optimum frequency resolution or the effective width of the spectrum group may be appropriately set in consideration of device characteristics, biological fluctuations, or the like of the blood pressure ratio calculation device.

Next, a processing procedure for calculating the maximum-minimum blood pressure ratio and calculating an absolute blood pressure waveform on the basis of the maximum-minimum blood pressure ratio in the absolute blood pressure waveform calculation system 1 including the relative blood pressure waveform acquisition device 10 according to this embodiment will be described with reference to the flowchart of FIG. 10.

As a premise of this process, information indicating the notch point in the blood pressure waveform of the subject is recorded on the computer 20 in advance. When a connection is established using wireless communication between the computer 20 and the processing unit 30 of the relative blood pressure waveform acquisition device 10, the information indicating the notch point of the subject is transmitted from the computer 20 to the absolute blood pressure waveform reproduction unit 35. Accordingly, the absolute blood pressure waveform reproduction unit 35 acquires the blood pressure value at the notch point of the subject.

Figure 10:
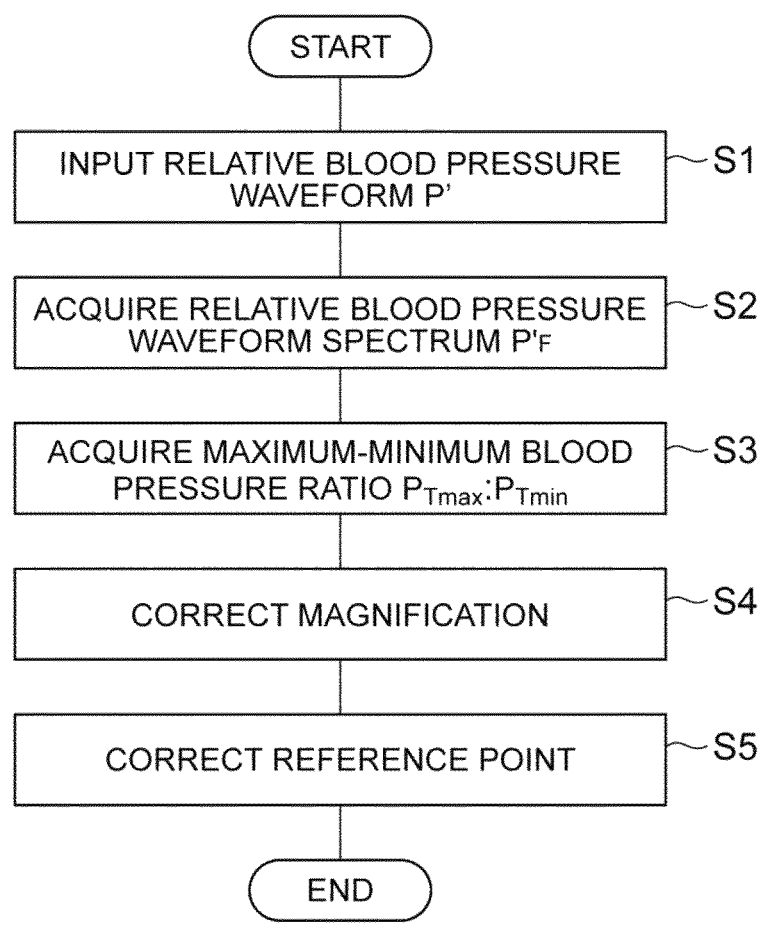
FIG. 10 is a flow diagram illustrating a processing procedure in an absolute blood pressure waveform calculation system.

As illustrated in FIG. 10, first, the relative blood pressure waveform P' is input by the input unit 32 on the basis of the signal from the detection unit 11 (S1: input step). Subsequently, the frequency domain representation conversion unit 33 performs Fourier transform on the relative blood pressure waveform P' acquired in S1 to calculate the relative blood pressure waveform spectrum P'$_F$ (S2: spectrum generation step). Subsequently, the maximum-minimum blood pressure ratio calculation unit 34 calculates the maximum-minimum blood pressure ratio P$_{Tmax}$:P$_{Tmin}$ on the basis of the relative blood pressure waveform spectrum P'$_F$ calculated in S2 using Equation (1) or Equation (2) (S3: analysis step). Through the processes of S1 to S3, the maximum-minimum blood pressure ratio P$_{Tmax}$:P$_{Tmin}$ is calculated.

Subsequently, the absolute blood pressure waveform reproduction unit 35 calculates the absolute blood pressure waveform P$_T$ by performing the correction process of S4 and S5 on the basis of the maximum-minimum blood pressure ratio P$_{Tmax}$:P$_{Tmin}$ calculated in S1 to S3. The absolute blood pressure waveform reproduction unit 35 performs correction of the magnification on the relative blood pressure waveform P' input in S1 (S4: absolute blood pressure waveform calculation step). That is, the absolute blood pressure waveform reproduction unit 35 detects a minimum point and a maximum point in the relative blood pressure waveform P', calculates a ratio between the detected minimum point and the detected maximum point, and corrects the magnification in the relative blood pressure waveform P' by adding an addition coefficient to the relative blood pressure waveform P' or multiplying the relative blood pressure waveform P' by a multiplication coefficient so that the ratio is substantially the same as the maximum-minimum blood pressure ratio P$_{Tmax}$:P$_{Tmin}$. Thus, the magnification-corrected relative blood pressure waveform is calculated.

Subsequently, the absolute blood pressure waveform reproduction unit 35 performs correction of the reference point on the magnification-corrected relative blood pressure waveform calculated in S4 (S5: absolute blood pressure waveform calculation step). That is, the absolute blood pressure waveform reproduction unit 35 detects the reference point in the magnification-corrected relative blood pressure waveform calculated in S4, and corrects the reference point in the magnification-corrected relative blood pressure waveform by adding an addition coefficient to the magnification-corrected relative blood pressure waveform or multiplying the magnification-corrected relative blood pressure waveform by a multiplication coefficient so that the waveform value of the detected reference point is substantially the same as that of the above-described notch point acquired from the computer 20. Accordingly, the absolute blood pressure waveform P$_T$ is calculated, and the process is ended. Information indicating the absolute blood pressure waveform P$_T$ calculated in S5 may be displayed, for example, on the display 20a of the computer 20 by being transmitted from the processing unit 30 to the computer 20.

Figure 11:
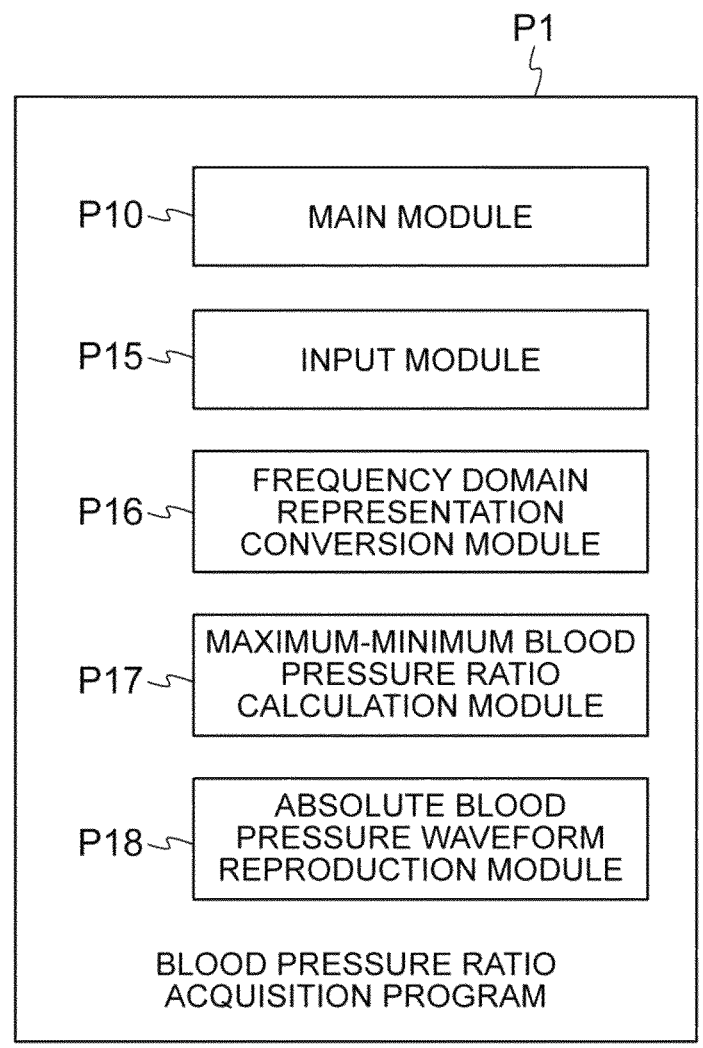
FIG. 11 is a diagram illustrating a configuration of a blood pressure ratio calculation program according to an embodiment of an aspect of the present invention.

Next, a blood pressure ratio calculation program for causing a computer to function as the relative blood pressure waveform acquisition device 10 will be described with reference to FIG. 11.

A blood pressure ratio calculation program P1 includes a main module P10, an input module P15, a frequency domain representation conversion module P16, a maximum-minimum blood pressure ratio calculation module P17, and an absolute blood pressure waveform reproduction module P18.

The main module P10 is a part that controls the entire blood pressure ratio calculation process. Functions realized by executing the input module P15, the frequency domain representation conversion module P16, the maximum-minimum blood pressure ratio calculation module P17, and the absolute blood pressure waveform reproduction module P18 are the same as those of the input unit 32, the frequency domain representation conversion unit 33, the maximum-minimum blood pressure ratio calculation unit 34, and the absolute blood pressure waveform reproduction unit 35 of the relative blood pressure waveform acquisition device 10.

The blood pressure ratio calculation program P1 is provided by, for example, a recording medium or a semiconductor memory such as a CD-ROM, a DVD or a ROM. Further, the blood pressure ratio calculation program P1 may be provided over a network as a computer data signal superimposed on a carrier wave.

As described above, according to the relative blood pressure waveform acquisition device 10 (blood pressure ratio calculation device), the blood pressure ratio calculation method, the blood pressure ratio calculation program P1, and the recording medium having the program recorded thereon of this embodiment, the maximum-minimum blood pressure ratio P$_{Tmax}$:P$_{Tmin}$ of the subject is calculated on the basis of the relative blood pressure waveform spectrum P'$_F$ generated by performing Fourier transform on the relative blood pressure waveform P'. Since the calculated maximum-minimum blood pressure ratio P$_{Tmax}$:P$_{Tmin}$ indicates one relationship between the relative blood pressure waveform and the absolute blood pressure, the blood pressure waveform, or the like, the absolute blood pressure waveform P$_T$ can be calculated from the relative blood pressure waveform P' using the maximum-minimum blood pressure ratio P$_{Tmax}$:P$_{Tmin}$. Therefore, by calculating the maximum-minimum blood pressure ratio P$_{Tmax}$:P$_{Tmin}$ on the basis of the relative blood pressure waveform P', it is possible to evaluate the cardiovascular system conveniently and accurately.

According to the maximum-minimum blood pressure ratio calculation unit 34, the maximum-minimum blood pressure ratio $P_{Tmax}:P_{Tmin}$ can be calculated on the basis of the relative blood pressure waveform spectrum $P'_F$ of the first harmonic wave or a higher harmonic wave. For example, the maximum-minimum blood pressure ratio calculation unit 34 can calculate the maximum-minimum blood pressure ratio $P_{Tmax}:P_{Tmin}$ on the basis of the sum of the intensities of the relative blood pressure waveform spectra $P'_F$ including the intensities of the respective relative blood pressure waveform spectra $P'_F$ of at least the first harmonic wave to the third harmonic wave. Further, the maximum-minimum blood pressure ratio calculation unit 34 can calculate the maximum-minimum blood pressure ratio $P_{Tmax}:P_{Tmin}$ on the basis of the sum of the intensities of the relative blood pressure waveform spectra $P'_F$ including the intensities of the respective relative blood pressure waveform spectra $P'_F$ of at least the first harmonic wave group to the third harmonic wave group.

Further, since the relative blood pressure waveform acquisition device 10 includes the detection unit 11 that acquires the relative blood pressure waveform P' of the subject and inputs the acquired relative blood pressure waveform P' to the input unit 32, it is possible to easily input the relative blood pressure waveform P' to the input unit 32 without providing a device that acquires the relative blood pressure waveform P' separately from the relative blood pressure waveform acquisition device 10.

Further, according to the relative blood pressure waveform acquisition device 10, it is possible to easily acquire the relative blood pressure waveform P' without providing a device that detects a signal for acquiring the relative blood pressure waveform P' separately from the relative blood pressure waveform acquisition device 10 by detecting the light radiated from the light source 11a of the detection unit 11 and transmitted through the inside of the living body H using the photodetector 11b of the detection unit 11.

Further, according to the relative blood pressure waveform acquisition device 10, the relative blood pressure waveform P' is corrected on the basis of the maximum-minimum blood pressure ratio $P_{Tmax}:P_{Tmin}$, and the absolute blood pressure waveform is calculated on the basis of the corrected relative blood pressure waveform P'. Accordingly, it is possible to accurately estimate the absolute blood pressure waveform $P_T$ from the relative blood pressure waveform P' and to evaluate the cardiovascular system on the basis of the estimated absolute blood pressure waveform $P_T$ conveniently, sufficiently, and accurately.

Second Embodiment

Next, an overview of a cardiac function evaluation system including a blood pressure ratio calculation device according to a second embodiment will be described. The cardiac function is a characteristic unique to each person and varies according to an environment. As an indicator for evaluating the cardiac function, there is a difference between the maximum blood pressure value and the minimum blood pressure value, a pulse pressure, or the like, and the pulse pressure is correlated with the maximum-minimum blood pressure ratio. According to this correlation, the cardiac function can be evaluated on the basis of the maximum-minimum blood pressure ratio. Therefore, in the cardiac function evaluation system according to this embodiment, the maximum-minimum blood pressure ratio of the absolute blood pressure waveform is obtained from the relative blood pressure waveform such as a photoelectric pulse wave, and a cardiac function is evaluated on the basis of the maximum-minimum blood pressure ratio.

Figure 12:
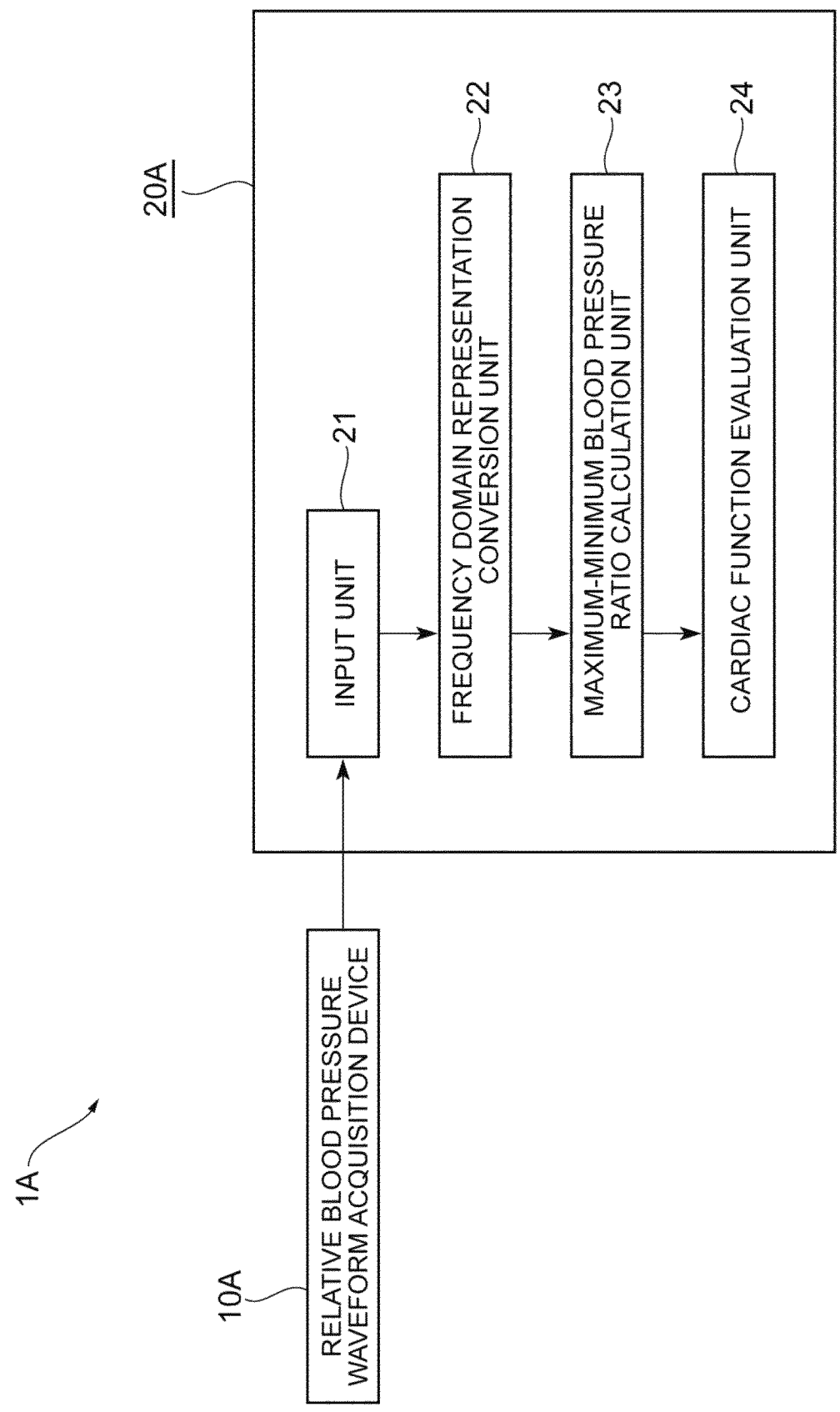
FIG. 12 is a functional block diagram of a cardiac function evaluation system according to a second embodiment.

FIG. 12 is a functional block diagram in the cardiac function evaluation system according to the second embodiment. As illustrated in FIG. 12, a cardiac function evaluation system 1A according to this embodiment includes a relative blood pressure waveform acquisition device 10A and a computer 20A (blood pressure ratio calculation device). The relative blood pressure waveform acquisition device 10A includes, for example, a Near Infra-Red Spectroscopy (NIRS) device, a pulse oximeter, a tonometer, a plethysmograph, an electromagnetic blood flow meter, an ultrasonic blood flow meter, a laser blood flow meter, or the like, and acquires the relative blood pressure waveform P'. The relative blood pressure waveform acquisition device 10A inputs the acquired relative blood pressure waveform P' to the computer 20A. A hardware configuration of the computer 20A according to this embodiment is realized by the same configuration as the hardware configuration illustrated in FIG. 3. Hereinafter, a functional configuration of the computer 20A will be described in detail.

The computer 20A according to this embodiment includes an input unit 21, a frequency domain representation conversion unit 22, a maximum-minimum blood pressure ratio calculation unit 23, and a cardiac function evaluation unit 24. The input unit 21 receives the relative blood pressure waveform P' from the relative blood pressure waveform acquisition device 10A. The input unit 21 outputs information on the input relative blood pressure waveform P' to the frequency domain representation conversion unit 22.

The frequency domain representation conversion unit 22 is a spectrum generation unit that generates a relative blood pressure waveform spectrum $P'_F$ by performing Fourier transform on the relative blood pressure waveform P' input by the input unit 21. That is, similarly to the frequency domain representation conversion unit 33 according to the first embodiment, the frequency domain representation conversion unit 22 converts the relative blood pressure waveform P' which is a function of time indicated in a time domain representation into a relative blood pressure waveform spectrum $P'_F$ which is a function of a frequency indicated in the frequency domain representation. The frequency domain representation conversion unit 22 outputs information on the generated relative blood pressure waveform spectrum $P'_F$ to the maximum-minimum blood pressure ratio calculation unit 23.

On the basis of the relative blood pressure waveform spectrum $P'_F$ equal to or higher than the frequency corresponding to the pulse of the subject in the relative blood pressure waveform spectrum $P'_F$ generated by the frequency domain representation conversion unit 22, the maximum-minimum blood pressure ratio calculation unit 23 calculates the maximum-minimum blood pressure ratio $P_{Tmax}:P_{Tmin}$ of the subject. Specifically, similar to the maximum-minimum blood pressure ratio calculation unit 34 according to the first embodiment, the maximum-minimum blood pressure ratio calculation unit 23 calculates the maximum-minimum blood pressure ratio $P_{Tmax}:P_{Tmin}$ on the basis of Equation (1) or (2) above. The maximum-minimum blood pressure ratio calculation unit 23 outputs the calculated maximum-minimum blood pressure ratio $P_{Tmax}:P_{Tmin}$ to the cardiac function evaluation unit 24.

The cardiac function evaluation unit 24 calculates the evaluation value of the cardiac function on the basis of the maximum-minimum blood pressure ratio $P_{Tmax}:P_{Tmin}$ calculated by the maximum-minimum blood pressure ratio calculation unit 23, and outputs the evaluation value of the cardiac function. The evaluation value of the cardiac function may be, for example, an amount of change from the maximum-minimum blood pressure ratio at the time of start of the measurement or may be a value that is calculated on the basis of a relationship created on the basis of statistical data in advance between the cardiac output and the maximum-minimum blood pressure ratio. The cardiac function evaluation unit 24 may display the evaluation value of the cardiac function on the display of the computer 20A.

A procedure of a process of calculating the maximum-minimum blood pressure ratio in the cardiac function evaluation system 1A including the computer 20A according to this embodiment is the same as the processes of S1 to S3 according to the first embodiment. The cardiac function evaluation unit 24 calculates an evaluation value of the cardiac function on the basis of the maximum-minimum blood pressure ratio $P_{Tmax}$:$P_{Tmin}$ calculated through the same processes as S1 to S3, and outputs the evaluation value of the cardiac function (cardiac function evaluation step). Thus, the process in the cardiac function evaluation system 1A ends.

Further, the blood pressure ratio calculation program for causing a computer to function as the computer 20A according to this embodiment is the same as the blood pressure ratio calculation program P1 according to the first embodiment, and includes a main module P10, an input module P15, a frequency domain representation conversion module P16, and a maximum-minimum blood pressure ratio calculation module P17, and includes a cardiac function evaluation module in place of the absolute blood pressure waveform reproduction module P18. A function realized by executing the cardiac function evaluation module is the same as the function of the cardiac function evaluation unit 24.

As described above, in this embodiment, the maximum-minimum blood pressure ratio $P_{Tmax}$:$P_{Tmin}$ of the subject is calculated on the basis of the relative blood pressure waveform spectrum $P'_F$ generated by performing Fourier transform on the relative blood pressure waveform P'. Therefore, the calculated maximum-minimum blood pressure ratio $P_{Tmax}$:$P_{Tmin}$ can be used as an evaluation index of the cardiac function. Therefore, by calculating the maximum-minimum blood pressure ratio $P_{Tmax}$:$P_{Tmin}$ on the basis of the relative blood pressure waveform P', it is possible to evaluate the cardiovascular system conveniently and accurately.

Further, in the cardiac function evaluation system 1A according to this embodiment, since the evaluation value of the cardiac function is acquired as an indicator for evaluating the cardiac function, the cardiovascular system can be evaluated on the basis of the acquired evaluation value conveniently, sufficiently, and accurately.

Although various embodiments of an aspect of the present invention have been described above, an aspect of the present invention is not limited to the above-described embodiments, and may be modified without departing from the gist described in each claim, or may be applied to others.

For example, in the absolute blood pressure waveform calculation system 1 according to the first embodiment, the relative blood pressure waveform acquisition device 10 is the blood pressure ratio calculation device, but the present invention is not limited thereto. For example, in the absolute blood pressure waveform calculation system 1, a configuration including the computer 20 in addition to the relative blood pressure waveform acquisition device 10 may be the blood pressure ratio calculation device, or the computer 20 may be the blood pressure ratio calculation device instead of the relative blood pressure waveform acquisition device 10, When the computer 20 is the blood pressure ratio calculation device, the computer 20 has the respective functions in the processing unit 30 described above. Further, for example, in the absolute blood pressure waveform calculation system 1, the computer 20 and the processing unit 30 may be integrally configured.

In the cardiac function evaluation system 1A according to the second embodiment, the computer 20A is the blood pressure ratio calculation device, but the present invention is not limited thereto. For example, in the cardiac function evaluation system 1A, a configuration including the relative blood pressure waveform acquisition device 10A in addition to the computer 20A may be the blood pressure ratio calculation device. The relative blood pressure waveform acquisition device 10 rather than the computer 20A may be the blood pressure ratio calculation device. When the relative blood pressure waveform acquisition device 10A is the blood pressure ratio calculation device, the relative blood pressure waveform acquisition device 10A has each function of the computer 20A described above.

Further, the maximum-minimum blood pressure ratio calculated by the absolute blood pressure waveform calculation system 1 may be used not only for calculation of the absolute blood pressure waveform, but also for evaluation of the cardiac function, for example. The maximum-minimum blood pressure ratio that is calculated by the cardiac function evaluation system 1A may be used not only for evaluation of the cardiac function, but also for calculation of the absolute blood pressure waveform, for example. The maximum-minimum blood pressure ratio calculated by the absolute blood pressure waveform calculation system 1 or the cardiac function evaluation system 1A is not limited to the calculation of absolute blood pressure waveform or the evaluation of the cardiac function, and may be used for evaluation of various other cardiovascular systems.

Figure 13:
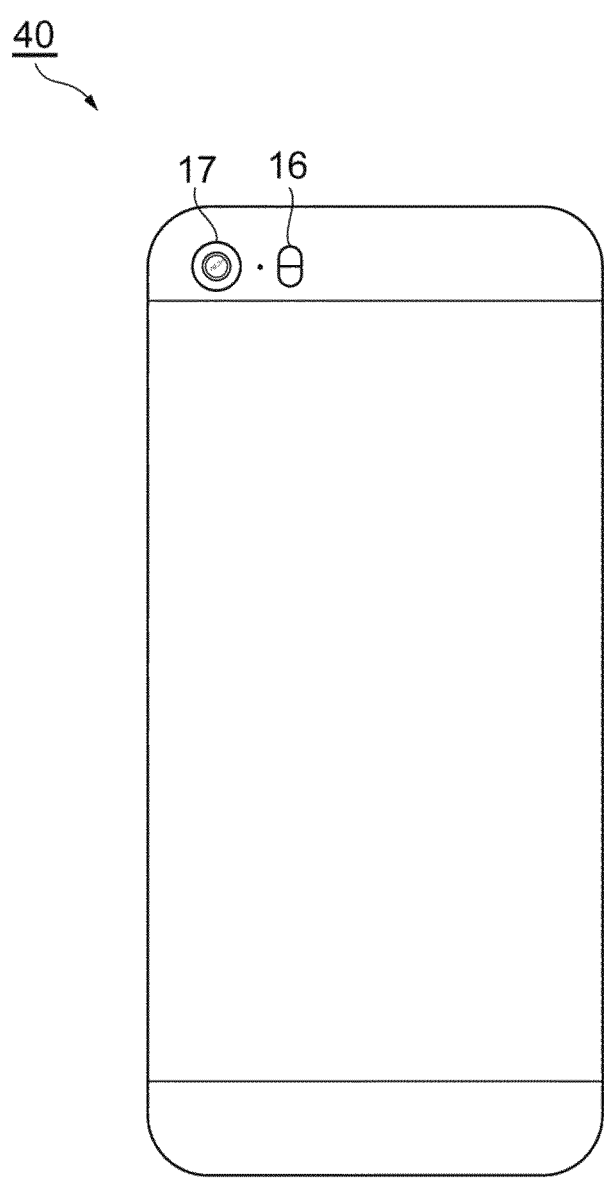
FIG. 13 is a schematic configuration diagram illustrating a blood pressure ratio calculation device according to a modification example.

Further, for example, as illustrated in FIG. 13, the blood pressure ratio calculation device may be configured as a communication terminal 40 such as a smartphone. The communication terminal such as a smartphone is included as a computer having a processor, a storage medium, and the like. In this case, the communication terminal 40 has, for example, the same function as each function of the relative blood pressure waveform acquisition device 10 or the computer 20A described above as a function of the blood pressure ratio calculation device. Further, the communication terminal 40 may have each function of the computer 20 in addition to each function of the relative blood pressure waveform acquisition device 10 or may have each function of the computer 20A in addition to each function of the relative blood pressure waveform acquisition device 10A. That is, each function of the relative blood pressure waveform acquisition device 10 and each function of the computer 20 according to the first embodiment may be realized in an integrated configuration, and each function of the computer 20A and each function of the relative blood pressure waveform acquisition device 10A according to the second embodiment may be realized in an integrated configuration.

The communication terminal 40 includes a flash lamp 16 (irradiation device) as a light source, and a camera 17 as a photodetector. The flash lamp 16 and the camera 17 are functions originally included in the communication terminal 40, for example. In this modification example, in a state in which a surface (for example, a finger) of a living body that is a subject is placed on both the flash lamp 16 and the camera 17, light from the flash lamp 16 is radiated from the surface of the living body to the inside thereof. Reflected light from the living body is detected by the camera 17 and acquired as a relative blood pressure waveform. Thus, the function originally included in the communication terminal 40 can also serve as the function of the acquisition unit that acquires the relative blood pressure waveform. The communication terminal 40 may include a light source and a photodetector for acquiring the relative blood pressure waveform, separately from the flash lamp 16 and the camera 17. Further, a tablet computer or the like is also included as a computer having a processor, a storage medium, and the like, and a tablet computer or the like may be used instead of the communication terminal 40.

Figure 14:
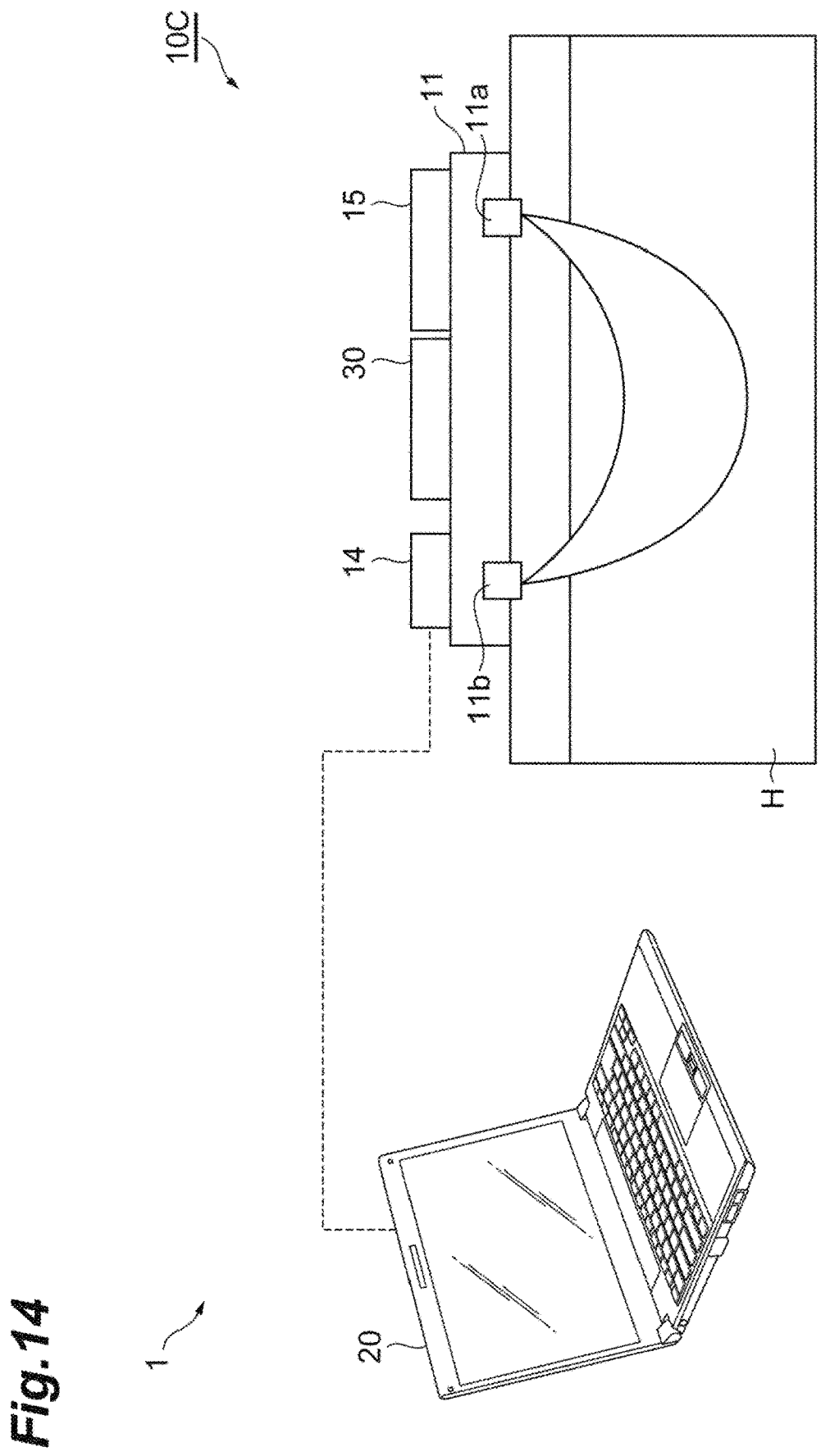
FIG. 14 is a schematic configuration diagram illustrating a blood pressure ratio calculation device according to a modification example.

Further, for example, as illustrated in FIG. 14, a relative blood pressure waveform acquisition device 10C in which the detection unit 11 and the processing unit 30 are integrated may be used as the relative blood pressure waveform acquisition device. The relative blood pressure waveform acquisition device 10C is attached to the surface of the living body H, and includes, for example, the communication unit 14, the processing unit 30, a power supply unit 15, and the detection unit 11 including the light source 11a and the photodetector 11b in an integrated manner.

Further, the surface of the living body that is the subject may be a part other than a palm or a finger, or may be the forehead, the upper arm, the neck, an earlobe, or the like.

Further, the present inventors have newly found that there is a statistically significant correspondence relationship between the relative blood pressure waveform spectrum at a frequency equal to or higher than the frequency corresponding to the pulse of an inspection target in the relative blood pressure waveform spectra generated by performing the Fourier transform on the relative blood pressure waveform, and have conceived that the maximum-minimum blood pressure ratio can be derived on the basis of the relative blood pressure waveform spectrum at a frequency equal to or higher than the frequency corresponding to the pulse of the inspection target. That is, in the blood pressure ratio calculation device according to the above embodiment, the analysis unit may calculate the maximum-minimum blood pressure ratio on the basis of the relative blood pressure waveform spectrum at a frequency equal to or higher than the frequency corresponding to the pulse of the inspection target. In the blood pressure ratio calculation method according to the above embodiment, in the analysis step, the maximum-minimum blood pressure ratio may be calculated on the basis of the relative blood pressure waveform spectrum at a frequency equal to or higher than the frequency corresponding to the pulse of the inspection target.

Further, the present inventors have conceived that, when the wave at the frequency corresponding to the pulse is set as the first harmonic wave and the wave at the frequency that is n times (n is a positive integer) the frequency of the first harmonic wave is set as an n-th harmonic wave in the relative blood pressure waveform spectrum, the maximum-minimum blood pressure ratio can be derived on the basis of the sum of the intensities of the relative blood pressure waveform spectra including the intensities of the respective relative blood pressure waveform spectra of at least the first harmonic wave to the third harmonic wave. That is, in the blood pressure ratio calculation device according to the above embodiment, when the wave at the frequency corresponding to the pulse is set as the first harmonic wave, and the wave at the frequency that is n times (n is a positive integer) the frequency of the first harmonic wave is set as an n-th harmonic wave in the relative blood pressure waveform spectrum, the analysis unit may calculate the maximum-minimum blood pressure ratio on the basis of the sum of the intensities of the relative blood pressure waveform spectra including the intensities of the respective relative blood pressure waveform spectra of at least the first harmonic wave to the third harmonic wave. Further, in the blood pressure ratio calculation method according to the above embodiment, when the wave at the frequency corresponding to the pulse is set as the first harmonic wave and the wave at a frequency that is n times (n is a positive integer) the frequency of the first harmonic wave is set as the n-th harmonic wave in the relative blood pressure waveform spectrum, the maximum-minimum blood pressure ratio may be calculated on the basis of the sum of the intensities of the relative blood pressure waveform spectra including the intensities of the respective relative blood pressure waveform spectra of at least the first harmonic wave to the third harmonic wave in the analysis step.

Further, the present inventors have conceived that, when a group of waves at a frequency in a predetermined range of the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the relative blood pressure waveform spectrum, the maximum-minimum blood pressure ratio can be derived on the basis of the sum of the intensities of the relative blood pressure waveform spectra including intensities of the respective relative blood pressure waveform spectra of at least the first harmonic wave group to the third harmonic wave group by setting the intensities of the respective spread n-th harmonic waves as the intensities of the n-th harmonic wave group even when each n-th harmonic wave is spread in a Gaussian shape in a frequency direction due to an influence of biological fluctuations. That is, in the blood pressure ratio calculation device according to the above embodiment, when a group of waves at a frequency in a predetermined range of the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the relative blood pressure waveform spectrum, the analysis unit may calculate the maximum-minimum blood pressure ratio on the basis of the sum of the intensities of the relative blood pressure waveform spectra including intensities of the respective relative blood pressure waveform spectra of at least the first harmonic wave group to the third harmonic wave group. Further, in the blood pressure ratio calculation method according to the above-described embodiment, when a group of waves at a frequency in a predetermined range of the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the relative blood pressure waveform spectrum, the analysis step may include calculating the maximum-minimum blood pressure ratio on the basis of the sum of the intensities of the relative blood pressure waveform spectra including intensities of the respective relative blood pressure waveform spectra of at least the first harmonic wave group to the third harmonic wave group.

The blood pressure ratio calculation device according to the above embodiment may further include an acquisition unit for acquiring the relative blood pressure waveform of the inspection target and inputting the acquired relative blood pressure waveform to the input unit. In this case, it is possible to easily input the relative blood pressure waveform to the input unit without providing a device that acquires the relative blood pressure waveform separately from the blood pressure ratio calculation device.

In the blood pressure ratio calculation device according to the above embodiment, the acquisition unit may include an irradiation device for irradiating the inside of the living body with light, and a photodetector for detecting the light transmitted through the inside of the living body. In this case, by detecting the light radiated from the irradiation device included in the acquisition unit, which has been transmitted through the inside of the living body, using the photodetector included in the acquisition unit, it is possible to easily acquire the relative blood pressure waveform without providing a device that detects a signal for acquiring the relative blood pressure waveform separately from the blood pressure ratio calculation device.

The blood pressure ratio calculation device according to the above embodiment may further include a blood pressure waveform calculation unit for calculating an absolute blood pressure waveform corresponding to temporal change in an absolute value of a blood pressure of the inspection target on the basis of the relative blood pressure waveform and the maximum-minimum blood pressure ratio. Further, the blood pressure ratio calculation method according to the above embodiment may further include a blood pressure waveform calculation step of calculating an absolute blood pressure waveform corresponding to temporal change in an absolute value of a blood pressure of the inspection target on the basis of the relative blood pressure waveform and the maximum-minimum blood pressure ratio. In this case, for example, it is possible to correct the relative blood pressure waveform on the basis of the maximum-minimum blood pressure ratio, and to calculate the absolute blood pressure waveform on the basis of the corrected relative blood pressure waveform. Thus, it is possible to accurately estimate the absolute blood pressure waveform from the relative blood pressure waveform, and to evaluate the cardiovascular system conveniently, sufficiently, and accurately on the basis of the estimated absolute blood pressure waveform.

The blood pressure ratio calculation device according to the above embodiment may further include a cardiac function evaluation unit for calculating an evaluation value of the cardiac function of the inspection target on the basis of the maximum-minimum blood pressure ratio. Further, the blood pressure ratio calculation method according to the above embodiment may further include a cardiac function evaluation step of calculating an evaluation value of a cardiac function of the inspection target on the basis of the maximum-minimum blood pressure ratio. In this case, since the evaluation value of the cardiac function is calculated as an indicator for evaluating the cardiac function, it is possible to evaluate the cardiovascular system on the basis of the calculated evaluation value conveniently, sufficiently, and accurately.

INDUSTRIAL APPLICABILITY

According to an aspect of the present invention, by adopting and using the blood pressure ratio calculation device, the blood pressure ratio calculation method, the blood pressure ratio calculation program, and the recording medium having the program recorded thereon, it is possible to evaluate the cardiovascular system conveniently, sufficiently, and accurately.

REFERENCE SIGNS LIST 10, 10C: Relative blood pressure waveform acquisition device (blood pressure ratio calculation device)
10A: Relative blood pressure waveform acquisition device (acquisition unit)
11: Detection unit (acquisition unit)
11a: Light source (irradiation device)
11b: Photodetector
16: Flash lamp (irradiation device)
17: Camera (photodetector)
20A: Computer (blood pressure ratio calculation device)
21, 32: Input unit
22, 33: Frequency domain representation conversion unit (spectrum generation unit)
23, 34: Maximum-minimum blood pressure ratio calculation unit (analysis unit)
24: Cardiac function evaluation unit
35: Absolute blood pressure waveform reproduction unit (blood pressure waveform calculation unit)
40: Communication terminal (blood pressure ratio calculation device)
H: Body (inspection target)
P1: Blood pressure ratio calculation program

The invention claimed is:

1. A device for calculating a maximum-minimum blood pressure ratio corresponding to a ratio between a maximum blood pressure value and a minimum blood pressure value of an inspection target, the device comprising:
  a processor configured to receive a relative blood pressure waveform corresponding to temporal change in relative blood pressure of the inspection target as input,
  perform Fourier transform on the relative blood pressure waveform and generate a relative blood pressure waveform spectrum,
  calculate the maximum-minimum blood pressure ratio on the basis of the relative blood pressure waveform spectrum, and
  calculate an absolute blood pressure waveform corresponding to temporal change in an absolute value of a blood pressure of the inspection target on the basis of the relative blood pressure waveform and the maximum-minimum blood pressure ratio.

2. The device according to claim 1, wherein the processor calculates the maximum-minimum blood pressure ratio on the basis of the relative blood pressure waveform spectrum at a frequency equal to or higher than a frequency corresponding to a pulse of the inspection target.

3. The device according to claim 2,
  wherein when a wave at the frequency corresponding to the pulse is set as a first harmonic wave and a wave at a frequency that is n times (n is a positive integer) the frequency of the first harmonic wave is set as an n-th harmonic wave in the relative blood pressure waveform spectrum,
  the processor calculates the maximum-minimum blood pressure ratio on the basis of a sum of intensities of the relative blood pressure waveform spectra including intensities of the respective relative blood pressure waveform spectra of at least the first harmonic wave to a third harmonic wave.

4. The device according to claim 2,
wherein when a group of waves at a frequency in a predetermined range of the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the relative blood pressure waveform spectrum,
the processor calculates the maximum-minimum blood pressure ratio on the basis of a sum of intensities of the relative blood pressure waveform spectra including intensities of the respective relative blood pressure waveform spectra of at least the first harmonic wave group to a third harmonic wave group.

5. The device according to claim 1, further comprising:
an acquisition device configured to acquire the relative blood pressure waveform of the inspection target and inputting the acquired relative blood pressure waveform to the processor.

6. The device according to claim 5, wherein the acquisition device includes an irradiation device irradiating an inside of a living body with light, and a photodetector detecting the light transmitted through the inside of the living body.

7. A method of calculating a maximum-minimum blood pressure ratio corresponding to a ratio between a maximum blood pressure value and a minimum blood pressure value of an inspection target, the blood pressure ratio calculation method comprising:
receiving, with a processor, a relative blood pressure waveform corresponding to temporal change in relative blood pressure of the inspection target as input;
performing, with the processor, Fourier transform on the relative blood pressure waveform and generating a relative blood pressure waveform spectrum;
calculating, with the processor, the maximum-minimum blood pressure ratio on the basis of the relative blood pressure waveform spectrum; and
calculating, with the processor, an absolute blood pressure waveform corresponding to temporal change in an absolute value of a blood pressure of the inspection target on the basis of the relative blood pressure waveform and the maximum-minimum blood pressure ratio.

8. The method according to claim 7 including calculating, with the processor, the maximum-minimum blood pressure ratio on the basis of the relative blood pressure waveform spectrum at a frequency equal to or higher than a frequency corresponding to a pulse of the inspection target.

9. The method according to claim 8,
wherein when a wave at the frequency corresponding to the pulse is set as a first harmonic wave and a wave at a frequency that is n times (n is a positive integer) the frequency of the first harmonic wave is set as an n-th harmonic wave in the relative blood pressure waveform spectrum,
the method including calculating, with the processor, the maximum-minimum blood pressure ratio on the basis of a sum of intensities of the relative blood pressure waveform spectra including intensities of the respective relative blood pressure waveform spectra of at least the first harmonic wave to a third harmonic wave.

10. The method according to claim 8,
wherein when a group of waves at a frequency in a predetermined range of the frequency corresponding to the pulse, including the frequency corresponding to the pulse, is set as a first harmonic wave group, and a group of waves at a frequency in a predetermined range of the n-times frequency, including the frequency that is n times (n is a positive integer) the frequency corresponding to the pulse, is set as an n-th harmonic wave group in the relative blood pressure waveform spectrum,
the method including calculating, with the processor, the maximum-minimum blood pressure ratio on the basis of a sum of intensities of the relative blood pressure waveform spectra including intensities of the respective relative blood pressure waveform spectra of at least the first harmonic wave group to a third harmonic wave group.

11. A non-transitory computer-readable storage medium including computer-readable instructions for causing a computer to execute a process of calculating a maximum-minimum blood pressure ratio corresponding to a ratio of a maximum blood pressure value to a minimum blood pressure value of an inspection target, the process comprising:
inputting a relative blood pressure waveform corresponding to temporal change in relative blood pressure of the inspection target;
performing Fourier transform on the relative blood pressure waveform and generating a relative blood pressure waveform spectrum;
calculating the maximum-minimum blood pressure ratio on the basis of the relative blood pressure waveform spectrum; and
calculating an absolute blood pressure waveform corresponding to temporal change in an absolute value of a blood pressure of the inspection target on the basis of the relative blood pressure waveform and the maximum-minimum blood pressure ratio.

* * * * *